US011414646B2

(12) United States Patent
Kim et al.

(10) Patent No.: US 11,414,646 B2
(45) Date of Patent: Aug. 16, 2022

(54) COMPOSITION FOR PROMOTING MATURATION OF DENDRITIC CELL CONTAINING FUSION PROTEIN OF RV2299C AND ESAT-6

(71) Applicant: Quratis Inc., Seoul (KR)

(72) Inventors: Hwa-Jung Kim, Daejeon (KR); Han-Gyu Choi, Daejeon (KR); Sung Jae Shin, Gyeonggi-do (KR)

(73) Assignee: Quratis Inc., Seoul (KR)

( * ) Notice: Subject to any disclaimer, the term of this patent is extended or adjusted under 35 U.S.C. 154(b) by 660 days.

(21) Appl. No.: 16/204,436

(22) Filed: Nov. 29, 2018

(65) Prior Publication Data

US 2019/0153390 A1 May 23, 2019

Related U.S. Application Data

(63) Continuation of application No. PCT/KR2017/005892, filed on Jun. 7, 2017.

(30) Foreign Application Priority Data

Jun. 7, 2016 (KR) ........................ 10-2016-0070517

(51) Int. Cl.

| | |
|---|---|
| *A61K 38/16* | (2006.01) |
| *C07K 14/35* | (2006.01) |
| *C12N 5/0784* | (2010.01) |
| *A61P 37/04* | (2006.01) |
| *C12N 1/20* | (2006.01) |
| *A61K 39/00* | (2006.01) |

(52) U.S. Cl.
CPC ............ *C12N 5/0639* (2013.01); *A61K 38/16* (2013.01); *A61P 37/04* (2018.01); *C07K 14/35* (2013.01); *A61K 39/00* (2013.01); *C07K 2319/00* (2013.01); *C12N 2501/998* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 8,273,357 | B2 | 9/2012 | Hacohen et al. |
| 10,301,686 | B2 | 5/2019 | Kim |
| 2013/0210005 | A1 | 8/2013 | Kim |

FOREIGN PATENT DOCUMENTS

| | | | |
|---|---|---|---|
| JP | 2012-214407 | A | 11/2012 |
| KR | 2013-0039061 | A | 4/2013 |
| KR | 20130081715 | A | 7/2013 |
| WO | 2010-030049 | A1 | 3/2010 |

OTHER PUBLICATIONS

Bao, X. et al., "The adjuvant effect of chimeric flagellin fliC/esat," Abstract only, vol. 27(4):377-381 (2011).
Choi, H-G, et al., "Rv2299c, a novel dendritic cell-activating antigen of *Mycobacterium tuberculosis*, fused-ESAT-6 subunit vaccine confers improved and durable protection against the hypervirulent strain HN878 in mice," Oncotarget, vol. 8:19947-19967 (2017).
Park, P. et al., "Characterization of a Novel Antigen of *Mycobacterium tuberculosis* K strain and Its Use in Immunodiagnosis of Tuberculosis," Journal of Microbiology, vol. 52(10): 871-878 (2014).
Vo, Manh-Cuong, et al., "Dendritic cell vaccination with a toll-like receptor agonist derived from mycobacteria enhances anti tumor immunity," Oncotarget, vol. 6(32): 33781-33790 (2015).
Wang, X. et al., "Early Secreted Antigenic Target of 6-kDa Protein of *Mycobacterium tuberculosis* Primes Dendritic Cells to Stimulate Th17 and Inhibit Th1 Immune Responses," The Journal of Immunology, vol. 189:3092-3103 (2012).

*Primary Examiner* — G. R. Ewoldt
*Assistant Examiner* — Marianne DiBrino
(74) *Attorney, Agent, or Firm* — Bret E. Field; Bozicevic, Field & Francis LLP

(57) ABSTRACT

The present invention relates to a composition for inducing dendritic cell maturation and a method for maturing dendritic cells. More particularly, the present invention relates to a composition including a fusion protein of Rv2299c and ESAT-6, both derived from *M. tuberculosis*, as an active ingredient for inducing dendritic cell maturation, and a method for differentiating immature dendritic cells into dendritic cells by using the same. The method of the present invention can increase a dendritic cell immune response in the body.

11 Claims, 34 Drawing Sheets

Specification includes a Sequence Listing.

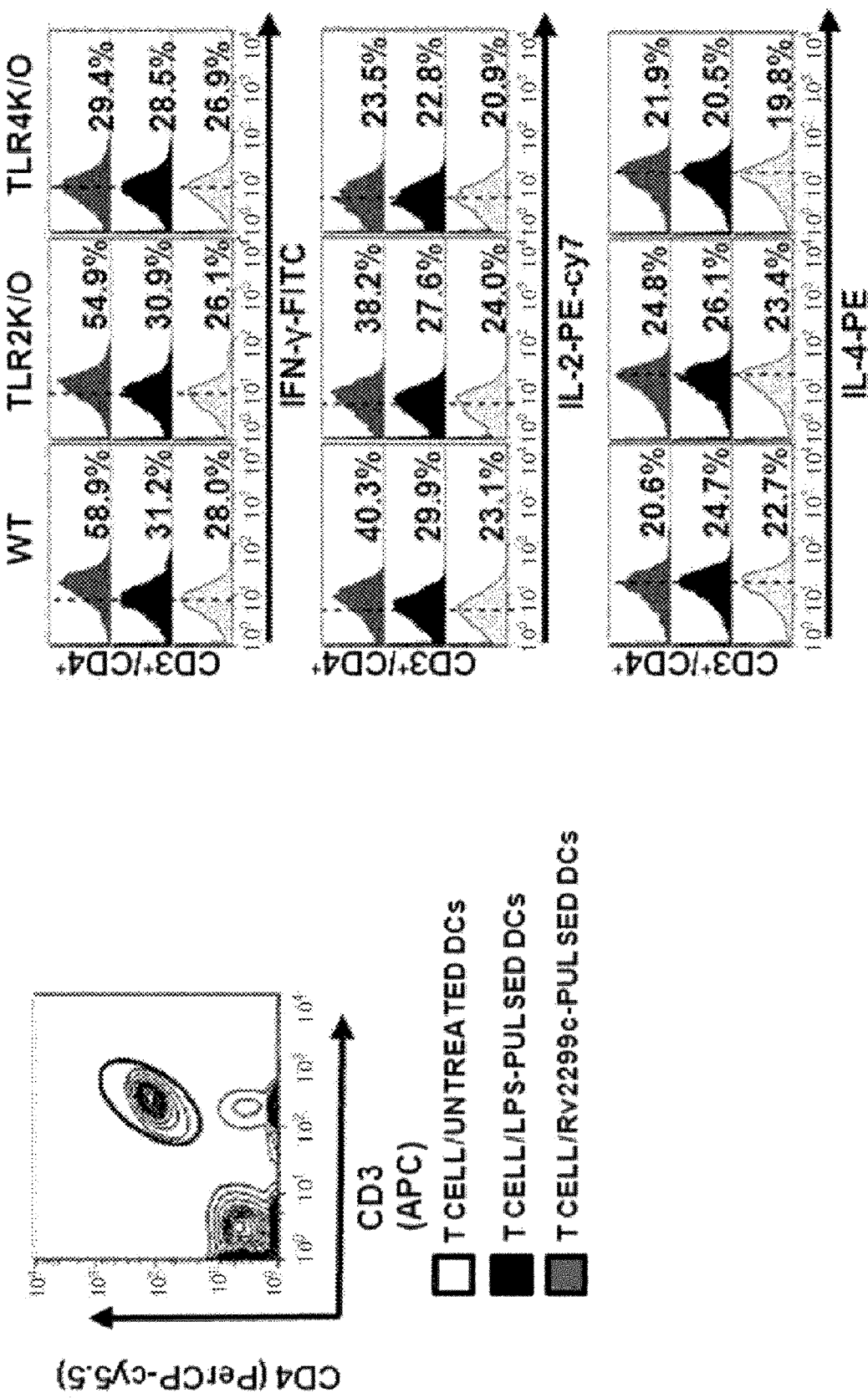

SEQUENCE LISTING

<160> NUMBER OF SEQ ID NOS: 5

<210> SEQ ID NO 1
<211> LENGTH: 647
<212> TYPE: PRT
<213> ORGANISM: Artificial Sequence
<220> FEATURE:
<223> OTHER INFORMATION: Rv2299c

<400> SEQUENCE: 1

```
Met Asn Ala His Val Glu Gln Leu Glu Phe Gln Ala Glu Ala Arg Gln
1               5                   10                  15
Leu Leu Asp Leu Met Val His Ser Val Tyr Ser Asn Lys Asp Ala Phe
            20                  25                  30
Leu Arg Glu Leu Ile Ser Asn Ala Ser Asp Ala Leu Asp Lys Leu Arg
        35                  40                  45
Ile Glu Ala Leu Arg Asn Lys Asp Leu Glu Val Asp Thr Ser Asp Leu
50                  55                  60
His Ile Glu Ile Asp Ala Asp Lys Ala Ala Arg Thr Leu Thr Val Arg
65                  70                  75                  80
Asp Asn Gly Ile Gly Met Ala Arg Glu Glu Val Val Asp Leu Ile Gly
                85                  90                  95
Thr Leu Ala Lys Ser Gly Thr Ala Glu Leu Arg Ala Gln Leu Arg Glu
            100                 105                 110
Ala Lys Asn Ala Ala Ser Glu Glu Leu Ile Gly Gln Phe Gly Ile
        115                 120                 125
Gly Phe Tyr Ser Ser Phe Met Val Ala Asp Lys Val Gln Leu Leu Thr
    130                 135                 140
Arg Lys Ala Gly Glu Ser Ala Ala Thr Arg Trp Glu Ser Ser Gly Glu
145                 150                 155                 160
Gly Thr Tyr Thr Ile Glu Ser Val Glu Asp Ala Pro Gln Gly Thr Ser
                165                 170                 175
Val Thr Leu His Leu Lys Pro Glu Asp Ala Glu Asp Leu His Asp
            180                 185                 190
Tyr Thr Ser Glu Trp Lys Ile Arg Asn Leu Val Lys Lys Tyr Ser Asp
        195                 200                 205
Phe Ile Ala Trp Pro Ile Arg Met Asp Val Glu Arg Arg Thr Pro Ala
210                 215                 220
Ser Gln Glu Glu Gly Glu Gly Gly Glu Glu Thr Val Thr Ile Glu
225                 230                 235                 240
Thr Glu Thr Leu Asn Ser Met Lys Ala Leu Trp Ala Arg Pro Lys Glu
                245                 250                 255
Glu Val Ser Glu Gln Glu Tyr Lys Glu Phe Tyr Lys His Val Ala His
            260                 265                 270
Ala Trp Asp Asp Pro Leu Glu Ile Ile Ala Met Lys Ala Glu Gly Thr
        275                 280                 285
Phe Glu Tyr Gln Ala Leu Leu Phe Ile Pro Ser His Ala Pro Phe Asp
    290                 295                 300
Leu Phe Asp Arg Asp Ala His Val Gly Ile Gln Leu Tyr Val Lys Arg
305                 310                 315                 320
Val Phe Ile Met Gly Asp Cys Asp Gln Leu Met Pro Glu Tyr Leu Arg
                325                 330                 335
Phe Val Lys Gly Val Val Asp Ala Gln Asp Met Ser Leu Asn Val Ser
            340                 345                 350
Arg Glu Ile Leu Gln Gln Asp Arg Gln Ile Lys Ala Ile Arg Arg Arg
        355                 360                 365
Leu Thr Lys Lys Val Leu Ser Thr Ile Lys Asp Val Gln Ser Ser Arg
    370                 375                 380
Pro Glu Asp Tyr Arg Thr Phe Trp Thr Gln Phe Gly Arg Val Leu Lys
385                 390                 395                 400
Glu Gly Leu Leu Ser Asp Ile Asp Asn Arg Glu Thr Leu Leu Gly Ile
                405                 410                 415
```

Ser Ser Phe Val Ser Thr Tyr Ser Glu Glu Pro Thr Thr Leu Ala
            420                 425                 430

Glu Tyr Val Glu Arg Met Lys Asp Gly Gln Gln Gln Ile Phe Tyr Ala
            435                 440                 445

Thr Gly Glu Thr Arg Gln Gln Leu Leu Lys Ser Pro His Leu Glu Ala
450                 455                 460

Phe Lys Ala Lys Gly Tyr Glu Val Leu Leu Leu Thr Asp Pro Val Asp
465                 470                 475                 480

Glu Val Trp Val Gly Met Val Pro Glu Phe Asp Gly Lys Pro Leu Gln
                485                 490                 495

Ser Val Ala Lys Gly Glu Val Asp Leu Ser Ser Glu Glu Asp Thr Ser
            500                 505                 510

Glu Ala Glu Arg Glu Glu Arg Gln Lys Glu Phe Ala Asp Leu Leu Thr
            515                 520                 525

Trp Leu Gln Glu Thr Leu Ser Asp His Val Lys Glu Val Arg Leu Ser
530                 535                 540

Thr Arg Leu Thr Glu Ser Pro Ala Cys Leu Ile Thr Asp Ala Phe Gly
545                 550                 555                 560

Met Thr Pro Ala Leu Ala Arg Ile Tyr Arg Ala Ser Gly Gln Glu Val
                565                 570                 575

Pro Val Gly Lys Arg Ile Leu Glu Leu Asn Pro Ser His Pro Leu Val
            580                 585                 590

Thr Gly Leu Arg Gln Ala His Gln Asp Arg Ala Asp Asp Ala Glu Lys
            595                 600                 605

Ser Leu Ala Glu Thr Ala Glu Leu Leu Tyr Gly Thr Ala Leu Leu Ala
610                 615                 620

Glu Gly Gly Ala Leu Glu Asp Pro Ala Arg Phe Ala Glu Leu Leu Ala
625                 630                 635                 640

Glu Arg Leu Ala Arg Thr Leu
                645

<210> SEQ ID NO 2
<211> LENGTH: 27
<212> TYPE: DNA
<213> ORGANISM: Artificial Sequence
<220> FEATURE:
<223> OTHER INFORMATION: Rv2299c forward primer

<400> SEQUENCE: 2
catatgaacg cccatgtcga gcagttg                                        27

<210> SEQ ID NO 3
<211> LENGTH: 29
<212> TYPE: DNA
<213> ORGANISM: Artificial Sequence
<220> FEATURE:
<223> OTHER INFORMATION: Rv2299c reverse primer

<400> SEQUENCE: 3
gaattcggca aggtacgcgc gagacgttc                                      29

<210> SEQ ID NO 4
<211> LENGTH: 27
<212> TYPE: DNA
<213> ORGANISM: Artificial Sequence
<220> FEATURE:
<223> OTHER INFORMATION: ESAT-6 forward primer

<400> SEQUENCE: 4

-continued

```
aagcttatga cagagcagca gtggaat                                        27

<210> SEQ ID NO 5
<211> LENGTH: 27
<212> TYPE: DNA
<213> ORGANISM: Artificial Sequence
<220> FEATURE:
<223> OTHER INFORMATION: ESAT-6 reverse primer

<400> SEQUENCE: 5
ctcgagtgcg aacatcccag tgacgtt                                        27
```

COMPOSITION FOR PROMOTING MATURATION OF DENDRITIC CELL CONTAINING FUSION PROTEIN OF RV2299C AND ESAT-6

CROSS-REFERENCE TO RELATED APPLICATIONS

This Applications is a continuation application of International Application No. PCT/KR2017/005892 filed on Jun. 7, 2017, which claims priority to Korean Application No. 10-2016-0070517 filed on Jun. 7, 2016. The applications are incorporated herein by reference.

TECHNICAL FIELD

The present invention relates to a composition for inducing maturation of dendritic cells and a method for maturing dendritic cells. More particularly, the present invention relates to a composition for inducing maturation of dendritic cell including fusion protein of ESAT-6 and Rv2299c derived from *M. tuberculosis* and a method of differentiating immature dendritic cells into mature dendritic cells using the same.

BACKGROUND ART

*Mycobacterium tuberculosis* (Mtb) is one of the most successful human pathogens, and one-third of the world's population is infected with *M. tuberculosis* (Kaufmann, 2001). Because *bovis* bacille Calmette-Guerin (BCG), which is the only vaccine currently in use, does not have a significant protective effect against tuberculosis (TB) (Brandt et al., 2002), a more effective vaccine that can replace or boost BCG is needed. For the development of promising tuberculosis (TB) vaccine candidates, it is crucial to identify and characterize mycobacterial antigens associated with prophylactic immune induction. However, many antigens have been used to generate TB vaccines currently in various stages of clinical trials (Ahsan, 2015).

The Th1 immune response is essential for the regulation of Mtb infection, which is evidenced by the increased susceptibility to mycobacterial infections in mice or humans with gene disruption or mutation associated with IFN-γ and IL-12 pathways (van Crevel et al., 2002). Accordingly, many studies on TB vaccines have focused on strong T cell stimulating antigens such as the antigen 85 complex (Ag85) and ESAT-6 (Yuk and Jo, 2014). Because T cell responses which are essential for controlling infection rarely remove Mtb from humans or animals infected (Feldman and Baggenstoss, 1938, Rhoades et al., 1997, Grace and Ernst, 2016), these antigens can induce strong prophylactic immunity, but have not been able to induce complete sterilization immunity (Weinrich Olsen et al., 2001, Aagaard et al., 2011).

Dendritic cells (DCs) are the most efficient antigen-presenting cells in the immune system, which are critical cells that act as a bridge between innate immunity and adaptive immunity.

Mtb manipulates the function of DC to delay the onset of T cell responses, thereby allowing the time for the microbes to proliferate (Gallegos et al., 2008, Hanekom et al., 2003, Wolf et al., 2007, Cooper, 2009). Thus, it suggests that the microbes survive in a dormant state. Accordingly, early activation of DC and DC migration to the lymph nodes as well as T cell stimulation are key factors in inducing effective prevention of Mtb infection. These results suggest that mycobacterial antigens, which induce effective host prophylactic immunity through DC activation, are promising targets for the development of TB vaccines. Indeed, DCs infected with BCG or exposed to the Mtb antigen showed significant preventive effects on normal and large amounts of virulent Mtb infection in mouse models. (Demangel et al., 1999, Rubakova et al., 2007). However, although several mycobacterial proteins which activate DCs to drive the Th1 immune response have been identified (Byun et al., 2012b), there is little known about their specific anti-tuberculosis immune mechanism and the protective effect of the protein as a vaccine.

If a fusion protein consisting of a DC-activated antigen and a T cell-stimulating antigen is used as a TB vaccine, this protein can provide two positive responses; Induction of Th1 polarization reaction by the DC-activated protein itself and prophylactic immunity improvement caused by T cell-stimulating antigen through DC activation. Therefore, it is assumed that the prophylactic effect of this fusion protein may be more effective than that of a vaccine including only T cell antigen. It has been reported that mycobacterial heat shock protein (HSP) such as HSP65 induces strong prophylactic immunity against TB or is effective as an adjuvant (Silva, 1999). In this study, we identified an Rv2299c protein, the HSP90 family that effectively induced DC maturation and examined the anti-tuberculosis immunity mechanism through DC activation leading to a robust Th1-type response. Next, we tested the prophylactic vaccine effect of Rv2299c protein or RV2299c-ESAT6 fused protein on Mtb HN878 clinical isolates. These results suggest that Rv2299c-mature DCs induce Th1 cell responses to anti-tuberculous immune activities, and a fusion protein including Rv2299c and ESAT-6 as a novel concept of the DC-activated protein-based vaccine is a promising vaccine target for boosting BCG.

SUMMARY

Since dendritic cells play a critical role in enhancing the immune function of the body itself as described above, the development of a non-toxic immunomodulator of inducing a robust immune response by promoting differentiation of dendritic cells to induce their maturation and a clear understanding of their mechanism of action is an important issue for cell immune treatment using dendritic cells.

Accordingly, an object of the present invention is to provide a composition for promoting maturation of dendritic cells.

Another object of the present invention is to provide a method for maturing dendritic cells.

Still another object of the present invention is to provide a therapeutic agent for *Mycobacterium tuberculosis* including dendritic cells matured by the method as described above.

In order to address the issues, the present invention provides a composition for activating dendritic cells, which includes a fusion protein of Rv2299c, which is based on Rv2299c protein, and ESAT-6 as an active ingredient.

Further, the present invention provides a composition for inducing maturation of dendritic cells in which the fusion protein of Rv2299c and ESAT-6 is a protein derived from *M. tuberculosis*.

The Rv2299c-ESAT-6 fusion protein is preferably included in a content of 1 μg/ml to 20 μg/ml.

Further, provided is a method for inducing maturation of immature dendritic cells by treating the immature dendritic cells with a fusion protein of Rv2299c and ESAT-6.

The method is preferable that after treating the immature dendritic cells with a fusion protein of Rv2299c and ESAT-6, the cells are cultured for 12 hours to 36 hours, and the fusion protein of Rv2299c and ESAT-6 is included in a content of 1 µg/ml to 20 µg/ml.

Provided is a method for inducing maturation of immature dendritic cells in which the fusion protein of Rv2299c and ESAT-6 increases the production of at least one selected from the group consisting of TNF-α, IL-12p70, IL-6 and IL-1β during the maturation of immature dendritic cells.

Further, in the present invention, the maturation of the immature dendritic cells is caused by stimulation of TLR (toll-like receptor)-4 with Rv2299c or stimulation of mitogen-activated protein kinase (MAPK) and NF-κB.

The dendritic cells produced by the method as described above are characterized by exhibiting positive immunological properties for a cluster of differentiation (CD) 80, CD86, major histocompatibility complex (MHC)-Class I and II.

Further, the present invention is to provide a composition for enhancing immunity, which includes the composition for inducing maturation of dendritic cells.

Immature cells can be well differentiated into mature dendritic cells by the method of maturing dendritic cells of the present invention so that the immune response of the body can be effectively activated.

BRIEF DESCRIPTION OF DRAWINGS

FIGS. 6A and 6B are graphs obtained using flow cytometry to determine whether Rv2299c-stimulated DC can stimulate CD4+.

FIGS. 11A, 11B, 12A and 12B are graphs illustrating that the changes in T cell phenotype induced by prophylactic inoculation with the fusion protein of Rv2299c and ESAT-6 were evaluated by cytokine staining and graphs illustrating IFN-γ, TNF-α and IL-2 co-expression and the like.

DETAILED DESCRIPTION

Figure 1A:
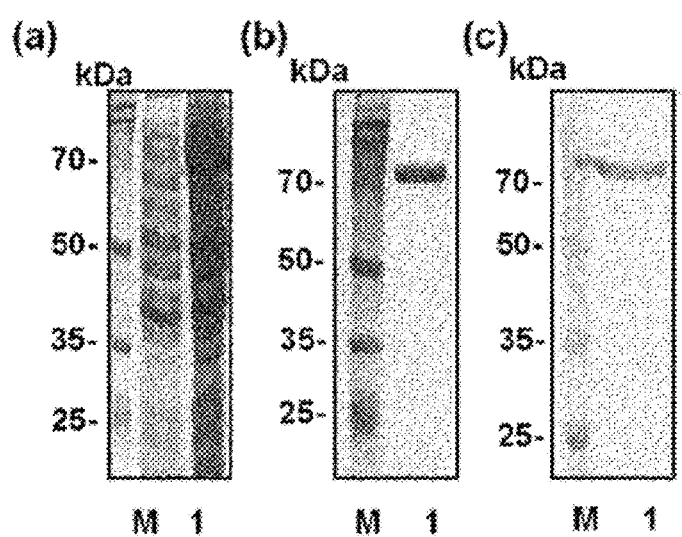
FIG. 1A is a view of SDS-PAGE and Western blot analysis for evaluating the purity of Rv2299c.

So far, a number of studies have been conducted on proteins derived from *M. tuberculosis* in the immune response to immunocytes, but studies on Rv2299c are not known.

Immature dendritic cells mature so as to form mature dendritic cells. Mature dendritic cells lose the ability to up-regulate expression of cell surface molecules and various cytokines that capture and simultaneously stimulate the antigen. Specifically, mature dendritic cells express MHC type I and type II antigens at higher levels compared to immature dendritic cells and regulate cluster of differentiation (CD) 80+, CD83+, CD86+ and CD14−. More MHC expression induces an increase in the antigenic density of dendritic cells, whereas up-regulation of CD80 and CD86, the co-stimulatory molecules, results in the improvement of a T cell activation signal through a co-stimulatory molecular counterpart such as CD28 on T cells.

The mature dendritic cells of the present invention may be prepared by contacting to Rv2299c or fusion protein of Rv2299c and ESTA-6 prepared by a recombinant method. The present invention may induce the maturation of dendritic cells through a composition including Rv2299c or a fusion protein of Rv2299c and ESTA-6. Rv2299c or a fusion protein of Rv2299c and ESTA-6 prepared by an effective recombinant method is not limited thereto, but the amount of Rv2299c may be included in the composition at a concentration of 1 μg/ml to 20 μg/ml, preferably 5 μg/ml to 10 μg/ml.

The maturation of dendritic cells may be monitored by methods known in the art. Cell surface markers may be detected with assays familiar to the art, such as flow cytometry and immunohistochemistry. The cells may also be monitored through cytokine production (e.g., ELISA, FACS, and other immunoassays).

Hereinafter, the present invention will be described in more detail with reference to Examples. The following Examples are provided to illustrate the present invention in a more easily understandable manner, and the present invention is not limited to Examples.

Example 1

Materials and Methods 1.1 Production of Bacterial Strain and *Mycobacterium* Genus Mtb H37Rv (ATCC 27294) and H37Ra (ATCC 25177) were purchased from an American strain bank (American Type Culture Collection, ATCC, Manassas, Va.), and Mtb HM878 was obtained from the International Tuberculosis Research Institute (ITRC, Changwon, Gyeongsangnam-do, South Korea). *Mycobacterium bovis* BCG (Pasteur strain 1173P2) was provided by Dr. Brooch of the Pasteur Institute (Paris, France). All mycobacteria used in these studies were prepared as described above (Cha et al., 2015b).

1.2 Animal, Vaccination and Aerosol Infection 5 to 6 weeks specific pathogen-free female C57BL/6 mice as well as OT-I and OT-II T-cell receptor (TCR) transformant mice (C57BL/6 background), C57BL/6 (H-2K$^b$ and I-A$^b$), C57BL/6J TLR2 knockout mice (TLR2$^{-/-}$; B6.129-Th2$^{tm1Kir}$/J) and C57BL/10 TLR4 knockout mice (TLR4$^{-/-}$; C57BL/10ScNJ) were purchased from The Jackson Laboratory (Bar Harbor, Me., USA). Mice were maintained at a constant temperature (24±1° C.) and humidity (50±5%) under the barrier conditions in the BL-3 biohazard animal facilities of the Yonsei University Medical Research Center. The animals were provided with a sterile commercial mouse diet as well as random access to water under standardized light control conditions (cycle of 12-hour light and 12-hour dark). Mice were monitored daily and none of the mice showed any clinical signs or illness during these experiments.

For vaccination, mice were first vaccinated with BCG Pasteur 1173P2 through subcutaneous injection (2.0×10$^5$ CFU/mouse). Six weeks after post-BCG immune vaccination, subunit vaccines were administered three times every three weeks as well as dimethyldioctadecylammonium (DDA) liposome (5 μg/injection) including monophosphoryl lipid-A (MPL, 5 μg/injection). Four weeks after the final immune vaccination, spleen and lung cells were harvested and used to investigate immunogenicity (levels of IFN-γ secretion and cycles of IFN-γ-producing T cells and Ag-specific T cells). In order to examine the prophylactic effect of the subunit vaccine alone, the BCG immunization alone and the BCG priming-subunit vaccine boosting group were challenged to generate a gas with Mtb H37Rv (ATCC 27294) or Mtb HN878 strains as described above (Cha et al., 2015b, Lee et al., 2009). To sum up, the mice were exposed to the inhalation chamber of an air-infected device (Glas-Col, Terre Haute, Ind., USA) for a period of 60 minutes with a given dose of H37Rv or HN878 in order to expose to Mtb having viable amount of about 200 CFU. At 8 or 16 weeks post-challenge, spleen and lung cells were harvested from respective groups, and flow cytometric analysis was used to evaluate the cycle of multifunctional T cells and T cell subtypes.

1.3 Antibody and Reagent

Recombinant mouse macrophage colony-stimulating factor (M-CSF), granulocyte-mouse macrophage colony factor (GM-CSF) and interleukin-4 (IL-4) were purchased from Creagene (Gyeonggi, South Korea). Fluorescein isothiocyanate (FITC)-Annexin V/propidium iodide kit was purchased from Research & Development System (Minneapolis, Minn., USA). Dextran-FITC (molecular weight, 40,000 Da) was obtained from Sigma (St. Louis, Mo., USA). Lipopolysaccharide from *E. coli* 0111:B4 was purchased from InvivoGen (San Diego, Calif., USA). Endotoxin filter (END-X) and endotoxin removal resin (END-X B15) were obtained from ACC (East Falmouth, Mass., USA). OT-I peptide (OVA$_{257-264}$) and OT-II peptide (OVA$_{323-339}$) were synthesized by a Peptron (Daejeon, South Korea). An anti-phosphorylated ERK1/2 monoclonal antibody, an anti-ERK1/2 monoclonal antibody, an anti-phosphorylated p38 monoclonal antibody, an anti-p38 monoclonal antibody, an anti-NF-κB (p65) polyclonal antibody, an anti-phosphorylated IκB-α monoclonal polyclonal antibody, an anti-IκB-a monoclonal antibody, an anti-lamin B polyclonal antibody, and an anti-13-actin polyclonal antibody were obtained from CST (Danvers, Mass., USA). An HRP-conjugated anti-mouse IgG antibody and an HRP-rhddor anti-rabbit antibody were obtained from Calbiochem (San Diego, Calif., USA), and anti-β-actin mAb (AC-15) was purchased from Sigma. CD11c, p65, IFN-g and CD62L-targeting FITC-conjugated mAbs, IL-12p70, IL-10 and CD3-targeting APC-conjugated mAb, CD4 and CD8-targeting PerCP-Cy5.5-conjugated mAb, CD8$^{+-}$ targeting APC-Cy7-conjugated mAb, CD80, CD86, MHC class I, MHC class II, IFN-γ and CD44-targeting phycoerythrin (PE)-conjugated mAb, CD11c and IL-2-targeting PE-Cy7-conjugated mAb, and CD3e-targeting eFluor 450-conjugated mAb were purchased from eBioscience (San Diego, Calif., USA). Phycoerythrin (PE)-conjugated mouse anti-IgG1, mouse anti-IgG2a and mouse anti-IgG2b, APC-conjugated mouse anti-IgG2a and mouse anti-IgG1, FITC-conjugated mouse anti-anti-IgG2b, and PE-Cy7-conjugated mouse anti-IgG1 and mouse anti-IgG2b were obtained from eBioscience (San Diego, Calif., USA). The antibodies were used as an isotype control. TNF-α, IFN-γ, IL-2, IL-4, IL-6, IL-10 and IL-12p70 ELISA kits were obtained from eBioscience.

1.4 Expression and Purification of Recombinant Protein

To produce the recombinant Rv2299c protein, the corresponding genes were amplified by polymerase chain reaction (PCR) using the *M. tuberculosis* H37Rv ATCC27294 genomic DNA as a template and the following primers: Rv2299c forward, 5'-<u>CATATG</u>AACGCCCATGTCGAG-CAGTTG-3' (SEQ. ID. No. 2), and reverse, 5'-<u>GAATTC</u>GGCAAGGTACGCGCGAGACGTTC-3' (SEQ. ID. No. 3), ESAT-6 forward, 5'-<u>AAGCTT</u>ATGACAGAG-CAGCAGTGGAAT-3' (SEQ. ID. No. 4), and reverse, 5'-<u>CTCGAG</u>TGCGAACATCCCAGTGACGTT-3' (SEQ. ID. No. 5). The PCR product of Rv2299c was digested with NdeI and EcoRI, and ESAT-6 was digested with HindIII and XhoI. These products were inserted into the pET22b (+) vector (Novagen, Madison, Wis., USA) and the result was sequenced. The recombinant plasmid was transformed into *E. coli* BL21 cells by thermal shock for 1 minute at 42° C. Over-expressed proteins were produced with slight modifications as described above (Cho et al., 2006). Briefly, *E. coli*-containing recombinant plasmids were incubated at 37° C. until the optical density (OD) thereof was 0.4-0.5 at 600 nm, and then they were induced by 1 mM isopropyl-D-thiogalactopyranoside (IPTG; ELPIS-Biotech, Daejeon, South Korea). The bacterial cells were then harvested by centrifugation and suspended in 20 mM Tris-HCl (pH 8.0), 0.5 M sodium chloride, 5 mM imidazole and 1 mM phenylmethylsulfonyl fluoride (Sigma); and dissolved by sonication. The recombinant proteins were purified by nickel-nitrilotriacetic acid (Ni-NTA) agarose chromatographic analysis according to the manufacturers instructions (Qiagen, Chatsworth, Calif., USA). The respective purification steps were analyzed by 13.5% sodium dodecyl sulfate polyacrylamide gel (SDS-PAGE) with Coomassie Brilliant Blue strain and immunoblot using anti-His antibody (Santa Cruz). The purified proteins were collected, concentrated and dialyzed for phosphate buffered saline (PBS, pH 7.4). In order to eliminate the endotoxin contamination, the dialyzed recombinant proteins were incubated with polymyxin B-agarose (PmB, Sigma) at 4° C. for 6 hours. Finally, the recombinant proteins without purified endotoxin were filtered and sterilized and frozen at −70° C. The protein concentrations were measured with a BCA protein assay kit (Pierce, Rockford, Ill.) using bovine serum albumin as a standard. The residual LPS of recombinant proteins was determined using the biological endotoxin (LAL) test (Lonza, Basel, Switzerland) according to the manufacturer's instructions. The purity of the recombinant proteins was evaluated by Coomassie Brilliant Blue (CB) staining and Western blot using anti-histidine antibodies.

1.5 Cell Culture

As recently described, murine bone marrow-derived DCs were produced, cultured, and purified (Byun et al., 2012b). Bone marrow-derived macrophages (BMDMs) were prepared using recombinant M-CSF as described above. Briefly, bone marrow cells isolated from C57BL/6 mice were dissolved with red blood cells (RBC) which dissolve buffer (4.15 g/500 ml of ammonium chloride and 0.01 M Tris-HCl buffer (pH 7.5±2)) and were washed with an RPMI 1640 medium. They were plated on a 6-well culture plate ($10^6$ cells/ml, 3 ml/well) and were cultured using an RPMI 1640 medium supplemented with 100 unit/ml of penicillin/streptomycin (Lonza), 10% fetal bovine serum (Lonza), 50 mM mercaptoethanol (Lonza), 0.1 mM non-essential amino acid (Lonza), 1 mM sodium pyruvate (Sigma), 20 ng/ml of GM-CSF and 10 ng/ml of IL-4 (BMDC) or 20 ng/ml of M-CSF (BMDM) at 37° C. in the presence of 5% carbon dioxide.

1.6 Cytotoxicity Analysis

Cytotoxicity assays were performed using the Annexin V/propidium iodide (PI) staining kit according to the manufacturer's instructions (BD Biosciences). Cells were stained with FITC-conjugated with Annexin V and PI. Analysis of stained cells was performed using FACSCanto II with FACSDiva, and the results were analyzed using FlowJo software (Tree Star, Ashland, Oreg., USA).

1.7 Analysis of Surface Molecule Expression by Flow Cell Analysis

On the 6th day, BMDCs were harvested, washed with PBS and resuspended in fluorescence activation cell sorbent wash buffer (2% FBS and 0.1% sodium azide in PBS). The cells were pre-cultured with 0.5% BSA in PBS for 30 minutes and washed with PBS. The cells were stained with FITC-conjugated anti-CD11c with PE-conjugated anti-H-2Kb (MHC class I), anti-I-antibody (MHC class II), anti-CD80 and anti-CD86 at 4° C. for 45 minutes. The cells were washed with PBS three times and resuspended with 500 µl of PBS. Fluorescence was measured by flow cytometry, and data were analyzed using CellQuest data analysis software.

1.8 Antibody Uptake Capacity of BMDC by Rv2299c

BMDCs ($2\times10^5$ cells) were maintained in equilibrium at 37° C. or 4° C. for 45 minutes and were pulsed at a concentration of 1 mg/ml with fluorescein-conjugated dextran. Cold dyeing buffer was added to stop the reaction. The cells were washed three times, stained with a PE-conjugated anti-CD11c antibody and then analyzed by FACSCanto. Non-specific binding of dextran to DC was determined by culturing DC with FITC-conjugated dextran at 4° C., and the resulting background values were subtracted from the specific binding values.

1.9 Identification of LPS-Contamination Removal for Rv2299c

In order to identify that the maturation of DCs induced by Rv2299c was not due to endotoxin contamination or LPS in protein preparations, pretreatment with polymyxin B (PmB) (Sigma), thermal denaturation, and proteinase K (Sigma) degradation were performed and analyzed. DC was pre-incubated with 50 µg/ml of PmB for 1 hour at room temperature before treatment with 100 ng/ml LPS and 10 ug/ml of Rv2299c. For the thermal denaturation, LPS or Rv2299c was incubated at 100° C. for 1 hour. For the degradation of proteinase K, LPS or Rv2299c was digested with soluble protease K at a concentration of 10 µg/ml at 37° C. for 1 hour. For the deactivation of enzymes, the enzymes were heated at 100° C. for 15 minutes and then added to the BMDC culture solution. After 24 hours, the levels of TNF-α and IL-6 in BMDC supernatants were analyzed using ELISA.

1.10 Confocal Scanning Laser Microscope

DCs were plated overnight on a poly-L-lysine-coated glass coverslip. After treatment with Rv2299c, the cells were fixed with 4% paraformaldehyde, permeabilized 0.1% Triton X-100. Before the cells were cultured with 2% BSA in anti-Rv2299c antibody including PBS/T at room temperature for 2 hours, the cells were blocked with 2% bovine serum albumin (BSA) in PBS including 0.1% Tween-20 (PBS/T) for 2 hours. After washing with PBS/T, the cells were re-cultured with Cy-3-conjugated secondary antibody in a dark room for 1 hour and then stained with 1 µg/ml of DAPI at room temperature for 10 minutes. Cell shape and fluorescence sensitivity were observed using a confocal laser microscope (Zeiss LSM 510 Meta; Carl Zeiss Ltd, Welwyn Garden City, UK). Their images were obtained using the LSM510 meta software and processed using an LSM image tester.

1.11 Immunoprecipitation

DCs ($1\times10^7$) were cultured with 10 mg/ml of Rv2299c for 6 hours, and the cell pellet was dissolved in lysis buffer (10 mM Tris-HCl (pH 7.4), 1% NP-40, 0.25% sodium deoxycholate, 150 mM HCl, 1 mM EDTA, 1 mM PMSF, 1 µg/ml of aprotinin, 1 µg/ml of leupeptin, 1 µg/ml of pepstatin, 1 mM $Na_3VO_4$, and 1 mM NaF). In order to prevent non-specific binding, 50 µl of normal serum (Santa Cruz) and 100 µl of 50% protein A or G-sepharose bead slurry (Invitrogen, Carlsbad, Calif.) were added to 1 mg of cell lysate to identify the stability of the cell lysate in advance. After incubation at 4° C. for 2 hours, the mixture of beads and cell lysate was centrifuged at 10,000×g at 4° C. for 5 minutes, and the supernatant was collected for the further experiment. Rv2299c (His), TLR2 and TLR4-related proteins were incubated with anti-mouse IgG as control antibodies for anti-TLR2 and TLR4 at 4° C. for 1 hour and with anti-mouse IgG as a control antibody for anti-Rv2299c(His), and then immunoprecipitated by incubation with protein A or G-sepharose at 4° C. for 24 hours. The beads were harvested, washed, and boiled in 5× sample buffer for 5 minutes. The proteins were separated on 10% SDS-PAGE and transferred to a vinylidene chloride difluoride membrane (Millipore). The membranes were further examined with anti-TLR2, TLR4 and His antibodies as described.

1.12 Immunoblotting Analysis

After stimulation with 10 µg/ml of Rv2299c, DCs were suspended in 100 µl of lysis buffer including 50 mM Tris-HCl (pH 7.5), 150 mM HCl, 1% Triton-X100, 1 mM EDTA, 50 mM NaF, 30 mM $Na_4PO_7$, 1 mM phenylmethane sulphonyl fluoride, 1 µg/ml of aprotinin and 1 mM pervanadate. Whole cell lysate samples were degraded in SDS-polyacrylamide gels and transferred to nitrocellulose membranes. The membranes were blocked with 5% skim milk, incubated with the antibody for 2 hours, and then incubated with HRP-conjugated secondary antibodies for 1 hour at room temperature. Epitopes on target proteins including MAPK and NF-κB which are specifically recognized for antibodies were visualized using an ECL advance kit (GE Healthcare, Little Chalfont, UK).

1.13 Production of Nuclear Extract

The nuclear extracts obtained from the cells were prepared as follows. DCs were treated with 100 ml of lysis buffer (10 mM HEPES (pH 7.9), 10 mM KCl, 0.1 mM EDTA, 0.5% Nonidet P-40, 1 mM dithiothreitol (DTT) and 0.5 mM PMSF) on ice for 10 minutes. After the centrifugation at 4,000 rpm for 5 minutes, the pellet was resuspended in 100 µl of extraction buffer (20 mM HEPES (pH 7.9), 40 mM sodium chloride, 1 mM EDTA, 1 mM DTT and 1 mM PMSF), the cells were cultured on ice for 30 minutes. After the centrifugation at 12,000 rpm for 10 minutes, the supernatant including the nuclear extracts was collected and stored at −80° C. until needed.

1.14 Treatment of DC with Pharmacological Inhibitor for Signaling Pathway Analysis All pharmacological inhibitors were purchased from Calbiochem. The dimethyl sulfoxide (Sigma) was added to the culture as a solvent control at 0.1% (vol/vol). DCs were washed with PBS and pretreated with inhibitors in an RPMI 1640 medium including glutamine for 1 hour before the treatment with Rv2299c for 24 hours. The inhibitors were used at the following concentrations: U0126 (10 µM), SB203580 (20 µM), SP600125 (10 µM) and Bay11-7082 (20 µM). In all experiments where inhibitors were used, test concentrations were determined after careful titration experiments to assess the viability of DCs using MTT assays.

1.15 In Vitro T Cell Proliferation Assay

Reactive T cells participating in the naive T cell response were isolated from total mononuclear cells prepared from BALB/c mice using a MACS column (Miltenyi Biotec). Both OVA-specific $CD8^+$ and $CD4^+$ reactive T cells, respectively were obtained from splenocytes from OT-1 and OT-2 mice. These T cells were stained with 1 µM CFSE (Invitrogen) as described above (Jeong et al., 2009). DCs ($2\times10^5$ cells per well) treated with OVA peptide for 24 hours in the presence of 10 µg/ml of Rv2299c were co-cultured with CFSE-stained $CD8^+$ and $CD4^+$ T cells ($2\times10^6$) at a DC to T cell ratio of 1:10. On the 3rd or 4th day from co-culture, the respective T cells were stained with PerCP-cy5.5-conjugated anti-$CD4^+$ mAb, PE-cy5-conjugated anti-$CD4^+$ mAb, PE-cy5-conjugated anti-$CD8^+$ mAb, Alexa647-conjugated anti-CCR3 mAb or PE-conjugated anti-CXCR3 mAb and analyzed by flow cytometer. The supernatants were harvested, and IFN-γ, IL-2 and IL-4 production was measured using ELISA.

1.16 Effect/Memory T Cell Activation Analysis

As described above, reactive T cells participating in allogeneic T cell response were isolated from total mononuclear cells prepared from *Mycobacterium*-infected BALB/c mice using a MACS column (Miltenyi Biotec). Staining with APC-conjugated anti-CD3 mAb (BD Biosciences) revealed that the preparation consisted mainly of $CD3^+$ cells (>95%). Large-scale DCs ($2\times10^5$ cells per well) prepared from wild-type (WT), $TLR2^{-/-}$ and $TLR4^{-/-}$ C57BL/6 mice after washing were treated with Rv2299c for 24 hours. The cells were co-cultured with $2\times10^6$ reactive allogeneic T cells at a ratio of T cell to DC of 1:10. On the 4th day of co-cultivation, the cells were stained with PerCP-cy5.5-conjugated anti-$CD4^+$ mAb, PerCP-cy5.5-conjugated anti-$CD8^+$ mAb, FITC-conjugated anti-CD62L mAb and PE-conjugated anti-CD44 mAb and analyzed by flow cytometer.

1.17 Measurement of Cytokine

The sandwich enzyme-linked immunosorbent assay (ELISA) was used to detect IL-6, IL-1β, TNF-α, IFN-γ, IL-4, IL-2, IL-12p70 and IL-10 in the culture supernatant as described above (Byun et al., 2012b). Single cells prepared from lungs of vaccinated or infected mice were stimulated with PPD (2 µg/ml) or antigen-specific CD4 or CD8 T cell peptides (2 µg/ml) at 37° C. for 24 hours. IFN-γ cytokine levels in culture supernatants were measured using a commercial ELISA kit (eBioscience) according to the manufacturer's protocol.

1.18 Analysis of Intracellular Cytokine

The cells were first blocked with 10% (vol/vol) normal goat serum at 4° C. for 15 minutes and stained with FITC-conjugated CD11c+antibodies at 4° C. for 30 minutes. The cells stained with the appropriate isotype-matched immunoglobulin (Ig) were used as a negative control. The cells were fixed and permeabilized with a Cytofix/Cytoperm kit (BD Biosciences) used according to the manufacturer's instructions. IL-12p70, IL-10, IL-2, IL-4 and IFN-γ in the cells were detected in permeation buffer with fluorescein-conjugated antibodies (BD Biosciences). Pure protein derivatives (PPD) were provided by Dr. Brennan of Aeras (Rockville, Md., USA). For intracellular cytokine staining, single-cell suspensions from vaccinated animals ($2\times10^6$ cells) were stimulated with PPD (2 µg/ml) and antigen-specific CD4 or CD8 T cell peptides (2 µg/ml) in the presence of GolgiStop at 37° C. for 12 hours (BD Biosciences). After the HN878 challenge, PPD was used alone as a stimulant for intracellular cytokine staining. The cells were first blocked with Fc block (anti-CD16/32) at 4° C. for 15 minutes and stained with BV421-conjugated anti-CD3, PerCp-Cy5.5-conjugated anti-CD4, APC-Cy7-conjugated anti-CD8 and FITC-conjugated anti-CD62L antibodies. The cells were fixed and permeabilized with a Cytofix/Cytoperm kit (BD Biosciences) used according to the manufacturer's instructions. TNF-α, IL-2 and IFN-γ in the cells were detected in permeation buffer using APC-conjugated anti-TNF-α, PE-Cy7-conjugated anti-IL-2 and PE-conjugated anti-IFN-γ antibodies. All antibodies were purchased from eBioscience (San Diego, Calif.) unless otherwise described. The cells were analyzed with FACSverse flow cytometry using a commercially available software program FlowJo (Treestar, Inc., San Carlos, Calif., USA).

1.19 Bacterial Count and Histopathological Analysis

After the final vaccination and then 16 weeks of the HN878 challenge, 6 to 7 mice per group were euthanized with carbon dioxide, and their lungs and spleen were homogenized. The viable counts were determined by plating on a Middlebrook 7H11 agar (Difco Laboratories, Detroit, Mich., USA) via serial dilution of the organ (half of the left lung and half of the spleen) homogenate, and were supplemented with 10% OADC (Difco Laboratories), Amphotericin B (Sigma-Aldrich, St. Louis, Mo., USA) and 2 μg/ml of 2-thiophenecarboxylic acid hydrazide (Sigma-Aldrich). Colonies were counted after incubation at 37° C. for 4 weeks. For histopathological analysis, the upper lobe of the right lung was stained with hematoxylin and eosin and evaluated for the severity of inflammation. As described above (Cha et al., 2015a), inflammatory levels in the lungs were assessed using the ImageJ (National Institutes of Health, Bethesda, ML) software program. Further, the inflammatory response was evaluated based on the size of the lesion and the composition of the immune cells. Data for CFU and pulmonary inflammation were reported as median $\log_{10}$ CFU±quadrant range (IQR).

1.20 Statistical Analysis

All experiments were repeated at least three times and consistent results were obtained. The significance level for the comparison between samples was determined by the distribution of Tukey's multiple comparison tests using a statistical software (GraphPad Prism Software, version 4.03; GraphPad Software, San Diego, Calif.). The data in the graph are expressed as means±SEM. Each value of $*p<0.05$, $p<0.01$ or $*p<0.001$ is considered statistically significant.

Example 2

Recombinant Rv2299c Protein Induces Maturation and Activation of Dendritic Cells (DCs).

Figure 1B:
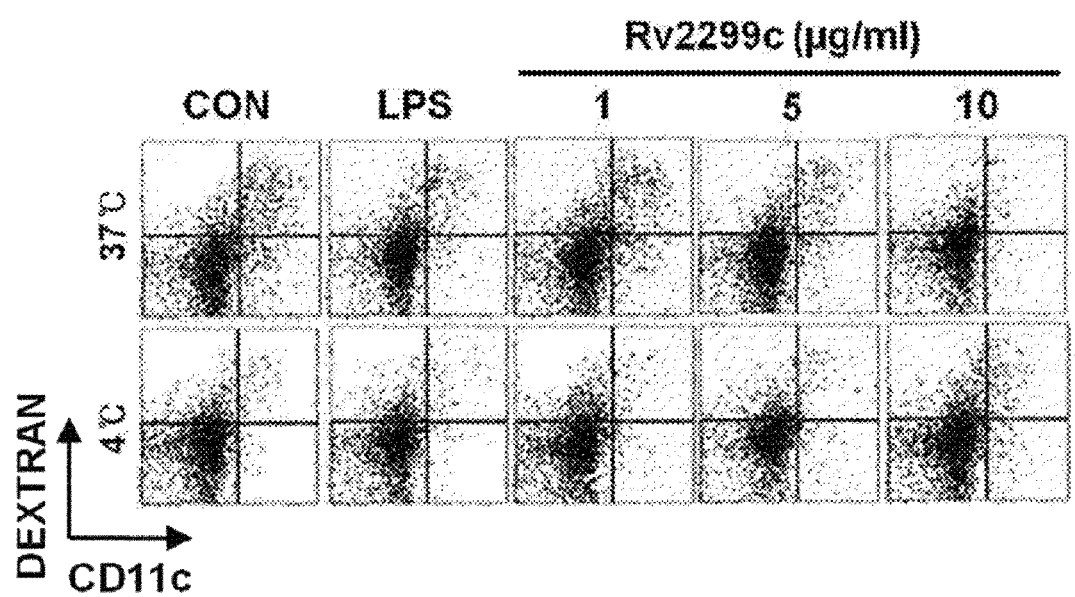
FIG. 1B is a view illustrating the reduction of the phagocytosis activity and the enhancement of the functional maturation due to proteins in DC treated with Rv2299c or LPS.
Figure 1C:
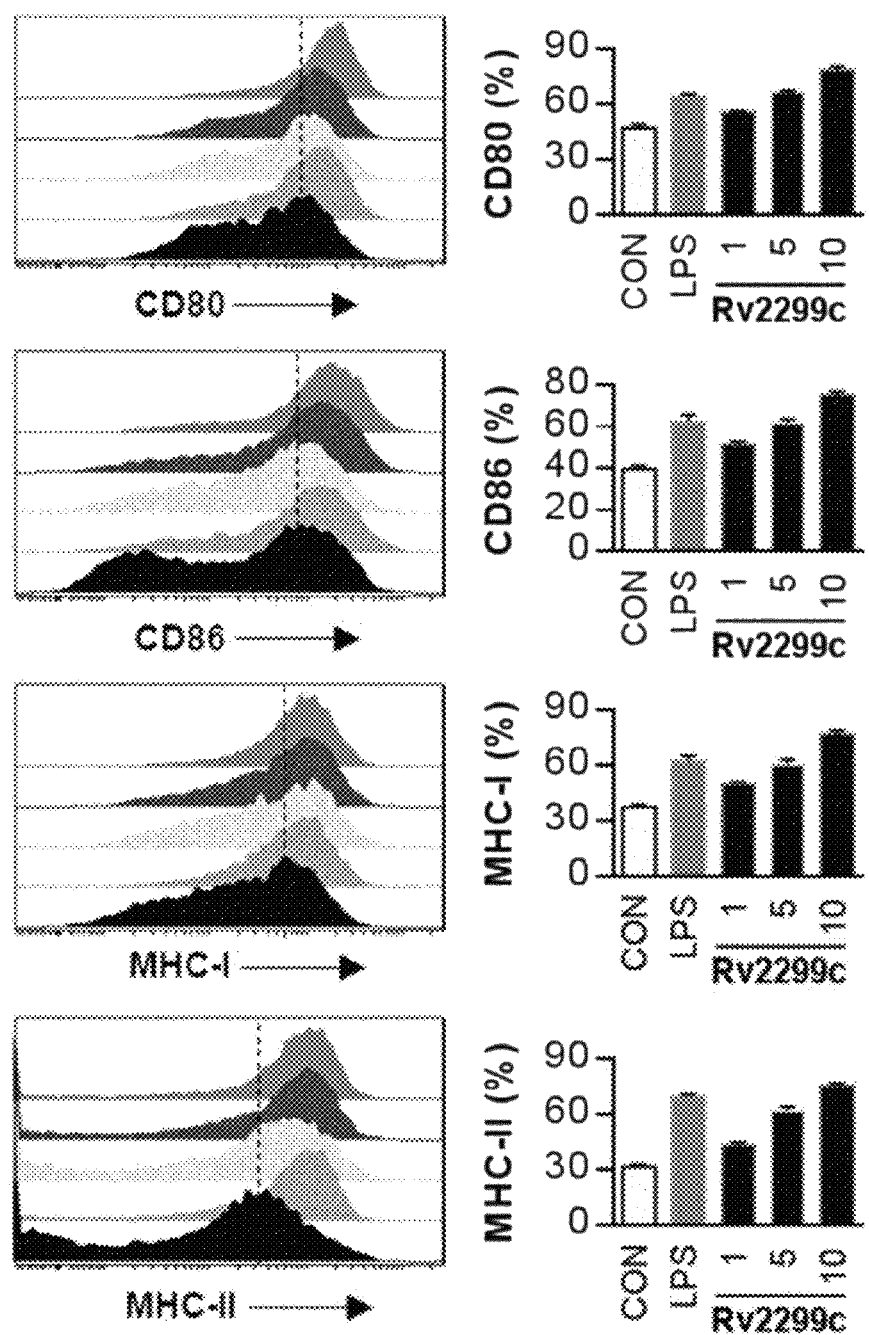
FIG. 1C is a view illustrating that the expression of class I and II molecules and co-stimulatory molecules such as CD80 and CD86 in DC treated with Rv2299c for 24 hours significantly increased dose-dependently.

2.1 Experimental Method (A) (a) Rv2299c was successfully induced in $E.$ $coli$ BL21 as a supplement of 1 mM isopropyl β-D-thiogalactoside (IPTG) for 6 hours. The proteins were mainly localized in inclusion bodies. The molecular weight of the N-terminal His-tag Rv2299c was close to 72 kDa by SDS-PAGE (M: molecular weight marker; lane 1: non-induction, lane 2: induction). Recombinant Rv2299c was produced in BL21 cells and purified with NTA resin. The purified proteins were subjected to (b) SDS-PAGE and (c) Western blot analysis using 1:1000 mouse anti-His antibodies. (B) BMDCs were treated with Rv2299c for 1, 5, or 10 μg/ml for 30 minutes, and then cultured in the absence or presence of LPS for 24 hours. The cells were cultured with dextran (FITC) at 37° C. for 30 minutes and then at 4° C. for 30 minutes and evaluated by FAC analysis of dextran (FITC) uptake. Dextran (FITC)-positive CD11c (PE)-positive cell proportion is shown. The results represent four experimental results. The bar graph shows the mean±SEM of dextran-FITC-positive CD11c+cell proportions for three independent experiments, and statistical significance ($***p<0.001$) is shown for the treatment as compared to the control. (C) BMDCs were cultured in the presence of 1, 5 or 10 μg/ml of Rv2299c for 24 hours and analyzed by two-color flow cytometry. The cells were gated to exclude CD11c cells. Medium: untreated control; LPS: positive control (100 μg/ml of LPS). DCs were stained with anti-CD80, anti-CD86, anti-MHC class I or anti-MHC class II. The results represent the three experimental results. The average fluorescence intensity was calculated from the above graph. Each bar represents the average fluorescence level of the sample. Data are presented as mean±SEM (n=5). $*p<0.05$, $p<0.01$ and $*p<0.001$ as compared to the untreated control group. (D) BMDCs were stimulated with 1, 5 or 10 μg/ml of Rv2299c and 100 ng/ml of LPS for 24 hours. Analysis of TNF-α, IL-6, IL-1β, IL-12p70 and IL-10 production was measured by ELISA. The results came from a representative experiment in one of the three experiments conducted. Data are presented as mean±SEM (n=5). $*p<0.05$, $p<0.01$ and $*p<0.001$ as compared to the untreated control group. (E) Analysis of IL-12p70 and IL-10 expression in CD11c+DC by intracellular cytokine staining 2.2 Analysis of Experimental Results There is little information about the immunological role of the Rv2299c protein in the mycobacterial HSP family. The recombinant Rv2299c proteins in $E.$ $coli$ BL21 were purified and examined their immune response. The purity of Rv2299c was evaluated by SDS-PAGE and Western blotting analysis (FIG. 1A). The endotoxin content of Rv2299c prepared was less than 15 pg/ml (<0.1 UE/ml) by LAL analysis. DCs and macrophages play an important role in the initiation and activation of prophylactic immune responses against mycobacteria. Thus, the effect of Rv2299c on macrophage activation or DC maturation was examined Rv2299c did not induce extra macrophage activation. As a marker for DC maturation, the phagocytosis activity was determined by exposing dextran-FITC. Double positive cells ($CD11c^+$ and dextran-FITC-positive) were reduced in DCs treated with Rv2299c or LPS used as a positive control, indicating decreased protein activity and enhanced functional maturation by the protein (See FIG. 1B) Further, DCs treated with Rv2299c for 24 hours significantly dose-dependently enhanced the expression of MHC class I and II molecules and co-stimulatory molecules such as CD80 and CD86 (See FIG. 1C). These results suggest that Rv2299c effectively induces DC maturation.

Figure 1D:
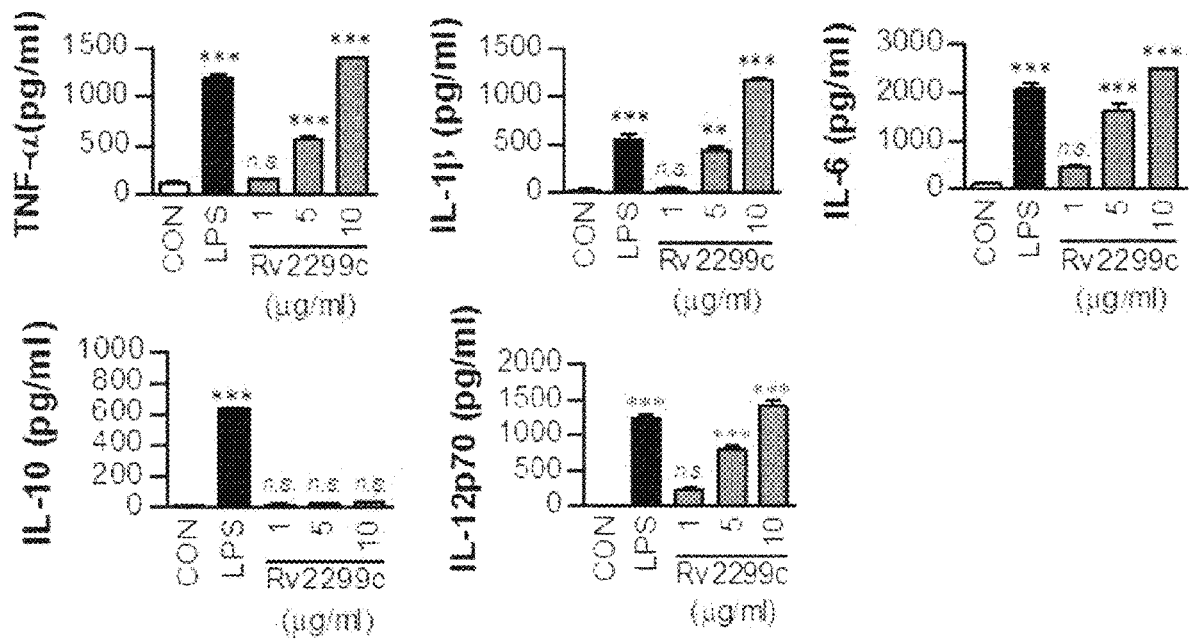
FIGS. 1D and 1E, respectively, are a graph and a view illustrating that the proportion of IL-12p70-positive cells significantly increased in DC treated with Rv2299c.
Figure 1E:
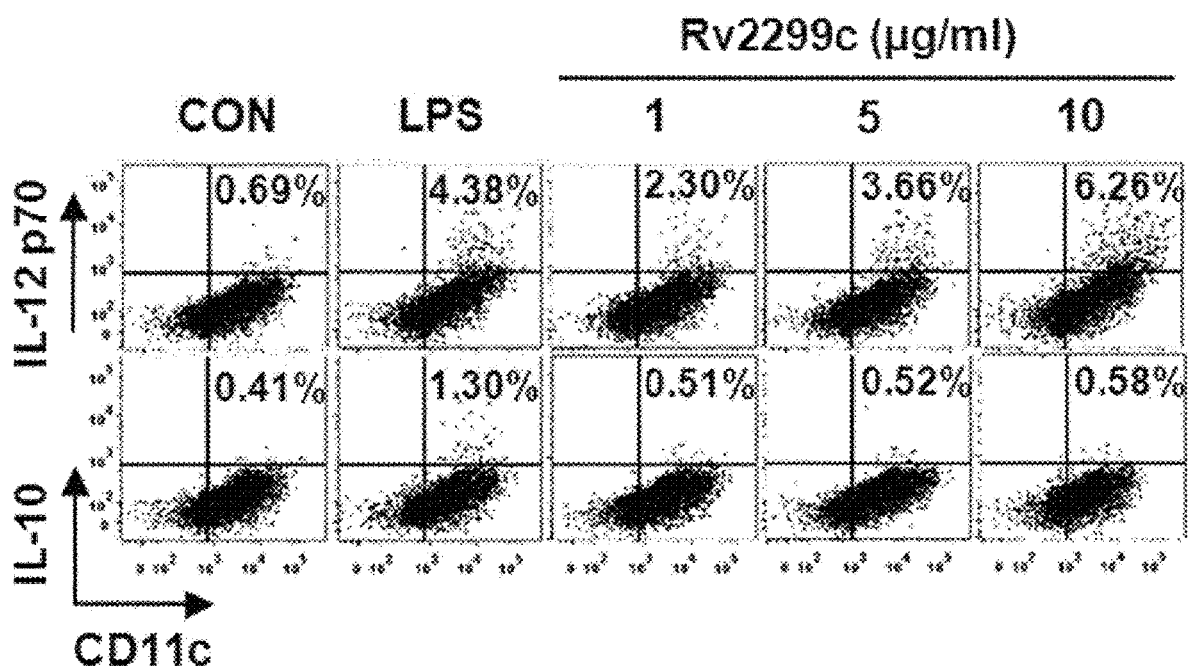
Figure 2:
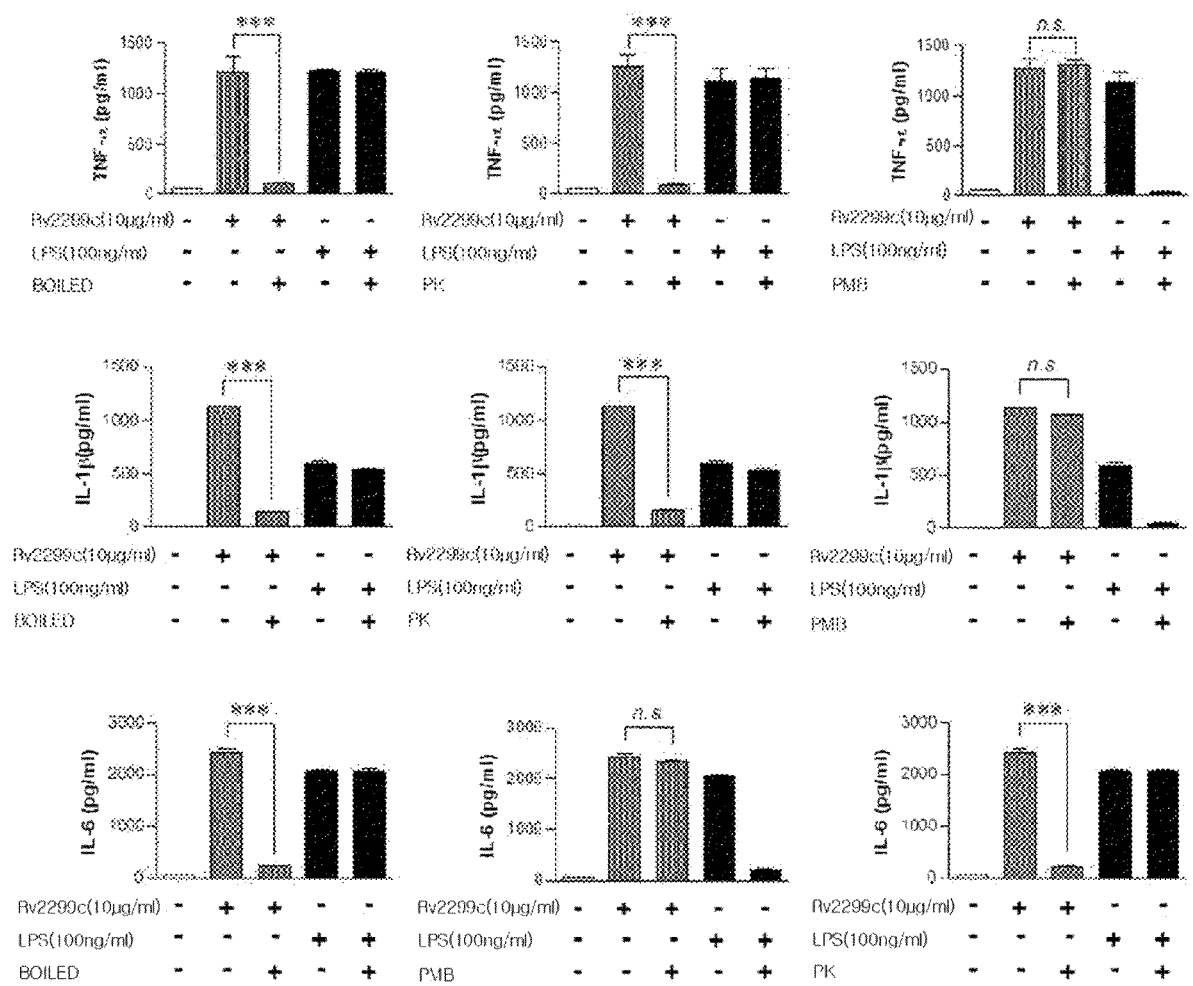
FIG. 2 is a graph illustrating the maturation activity of dendritic cells caused by Rv2299c is caused by endotoxin contamination.

Next, it was analyzed whether Rv2299c-mediated DC maturation was associated with the secretion of proinflammatory or anti-inflammatory cytokines. As illustrated in FIG. 1D, Rv2299c significantly stimulated DCs to secrete high levels of TNF-α, IL-6 and IL-1β, whereas untreated DCs secreted negligible cytokines. Then, the production of IL-12p70 and IL-10 with significant effects on T cell-mediated immune response development was determined. Unlike LPS, Rv2299c significantly induced secretion of IL-12p70 other than IL-10 (See FIG. 1D). FACS analysis showed that there was no change in IL-10 positive cells, but the proportion of IL-12p70-positive cells was increased in Rv2299c-treated DCs compared to the results obtained for untreated DCs (See FIG. 1E). Although the endotoxin content determined the total time to produce recombinant proteins, it was confirmed that Rv2299c ability to induce DC maturation was not due to LPS contamination through proteinase K or thermal denaturation treatment (See FIG. 2). Further, the polymyxin B treatment did not affect the activity of Rv2299c, but the activity of LPS was significantly inhibited by polymyxin B. In this view, these results suggest that Rv2299c induces proinflammatory cytokine secretion in DCs and that such Rv2299c-mature DCs may promote a Th1-type immune response.

Example 3

Rv2299c Induces the Maturation of Dendritic Cells (DCs) Through the TLR4 Pathway.

3.1 Experimental Method (A) The bar graphs show the expression of CD86 or MHCII in Rv2299c-treated CD11c+-gated DCs derived from WT, TLR2/and TLR4/mice. DCs derived from WT, TLR2/and TLR4/mice were treated with Rv2299c (10

μg/ml) for 24 hours. The proportion of positive cells is shown on each panel. The bar graph shows the mean±SEM of the proportion for each surface molecule to CD11c+ cells in three independent experiments. Statistical significance (*p<0.001) appears as Rv2299c-treated TLR2/versus Rv2299c-treated WT DC. All data are expressed as mean±SD (n=3), and statistical significance (*p<0.001) appears for the treatment as compared to Rv2299c-treated WT DC. (B) DCs derived from WT, TLR2/and TLR4/mice were treated with Rv2299c or LPS for 24 hours. Production of TNF-α, IL-6, or IL-1β in Rv2299c- or LPS-treated DCs derived from WT, TLR2/and TLR4/mice was measured by ELISA. All data are presented as mean±SD (n=3) and statistical significance (*p<0.001) is shown for the treatment as compared to Rv2299c-treated WT DC. (C) DCs derived from WT, MyD88/and TRIF/mice were treated with Rv2299c (10 μg/ml) and LPS (100 ng/ml) for 24 hours. Production of TNF-α, IL-6, or IL-1β in Rv2299c- or LPS-treated DCs derived from WT, MyD88/and TRIF/mice was measured by ELISA. All data are presented as mean±SD (n=3) and statistical significance (*p<0.001) is shown for the treatment as compared to Rv2299c-treated WT DC. (D) Fluorescence intensity of anti-Rv2299c combined with Rv2299c-treated DC. DCs derived from WT, TLR2/and TLR4/mice were treated with Rv2299c (10 μg/ml) for 1 hour, fixed and stained with DAPI and Cy3-conjugated anti-His antibodies (reference: 10 μM). (E) BMDCs derived from WT, TLR2/and TLR4/mice were treated with Rv2299c (10 μg/ml) for 1 hour and stained with Alexa488-conjugated anti-His mAb. The proportion of positive cells is shown on each panel. The bar graph shows the mean±SEM of Rv2299c-Alexa488 proportion in CD11c+ cells obtained from three independent experiments. Statistical significance (***p<0.001) appears for Rv2299c-treated TLR4/as compared to Rv2299c-treated WT DC. (F) Immunoprecipitation (IP) with anti-His, anti-TLR2 or anti-TLR4 antibodies and immunoblotting with anti-His, anti-TLR2 or anti-TLR4 antibodies. DCs were treated with Rv2299c (10 μg/ml) for 6 hours. The cells were harvested, and cell lysates were immunoprecipitated with anti-mouse IgG, anti-mouse IgG, anti-His, anti-TLR2 or anti-TLR4. The proteins were then visualized by immunoblotting with anti-His, anti-TLR2 or anti-TLR4 antibodies. The total indicates the average total cell lysate.

3.2 Analysis of Experimental Results

Figure 3A:
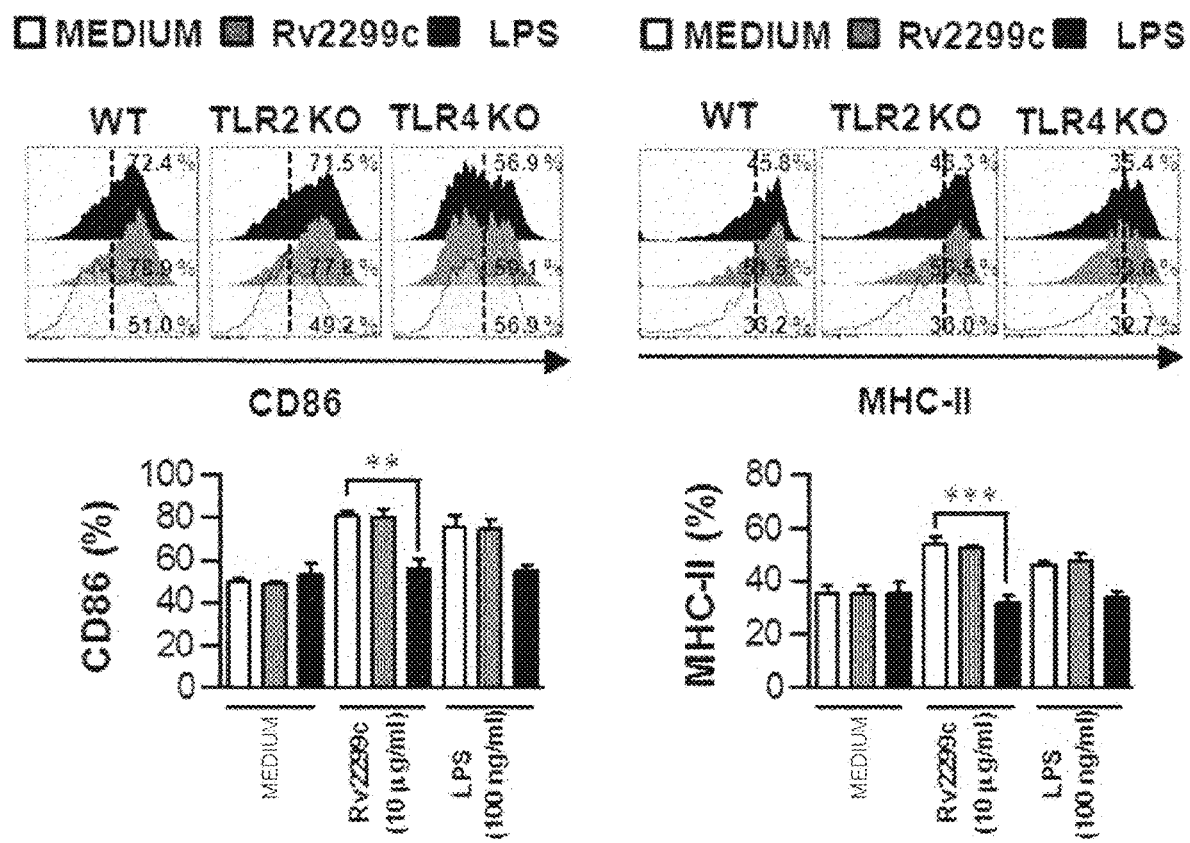
FIGS. 3A and 3B are graphs illustrating that Rv2299c activates DCs through the pathway by TLR4 to induce the expression of surface molecules and proinflammatory cytokines.
Figure 3B:
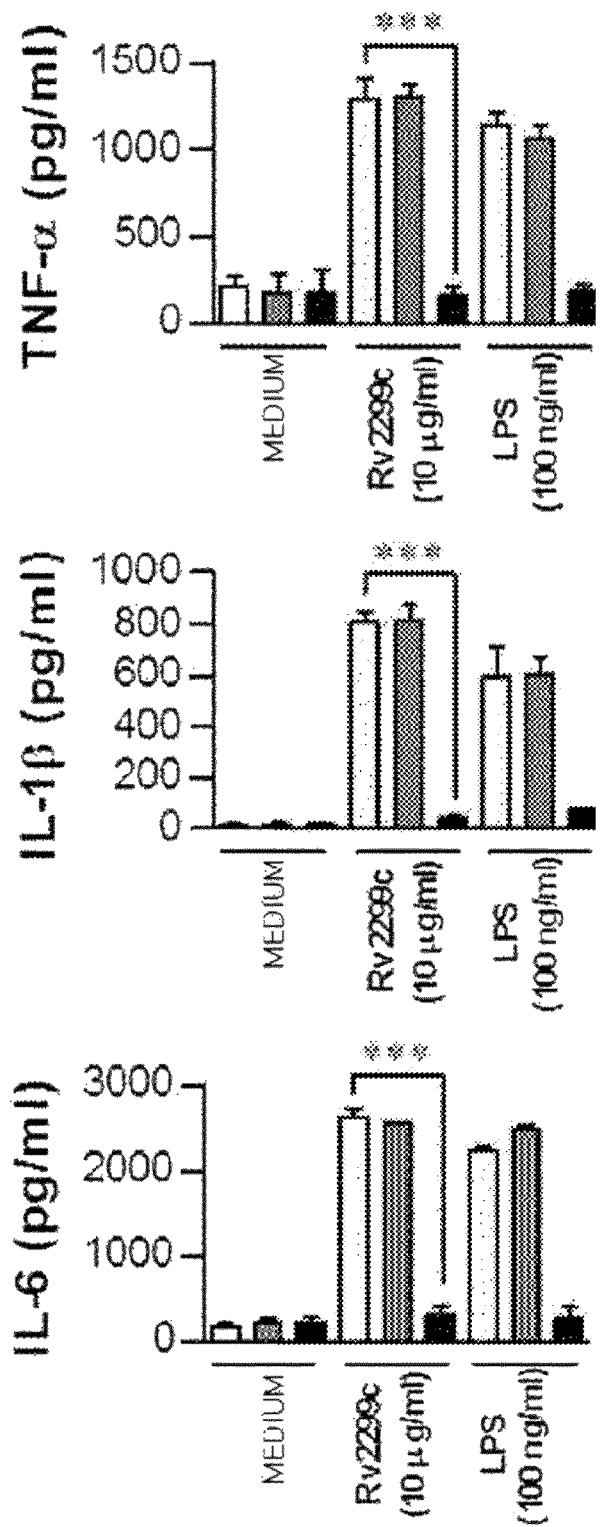
Figure 3C:
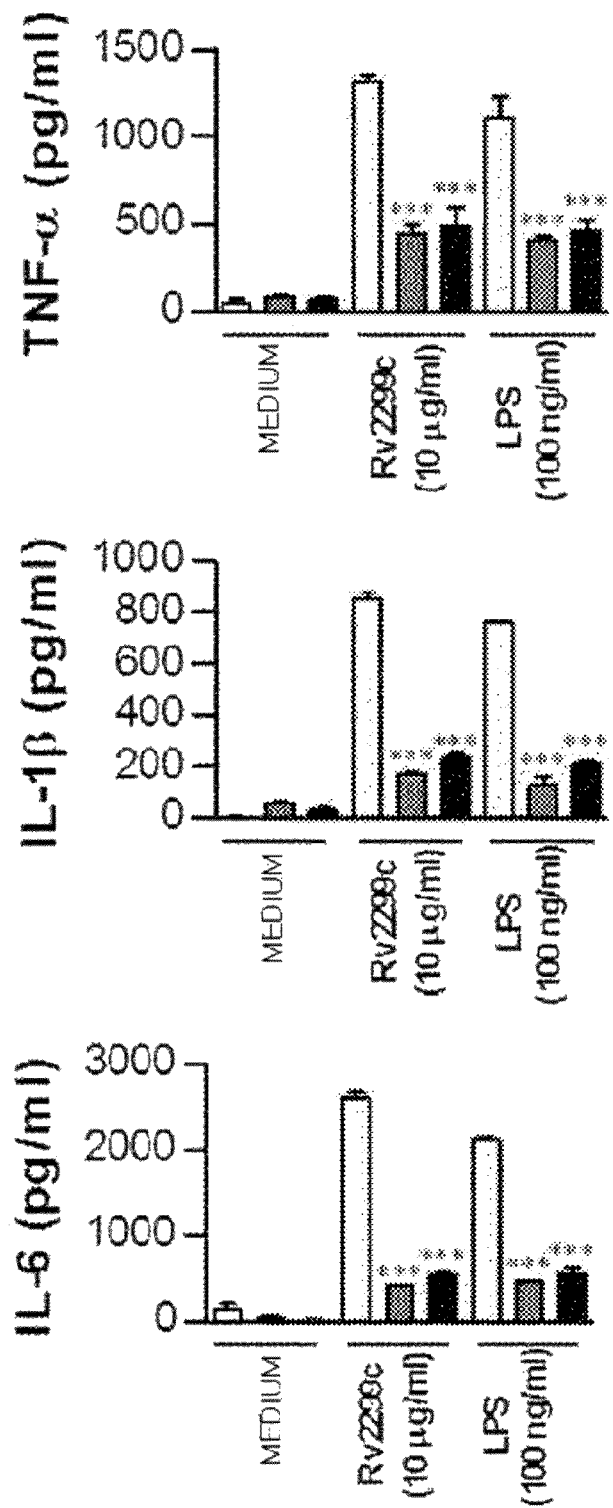
FIG. 3C is a graph illustrating that the production of cytokines (TNF-α, IL-6 and IL-1(3) in dendritic cells treated with Rv2299c is dependent on TRIF and MyD88.
Figure 3D:
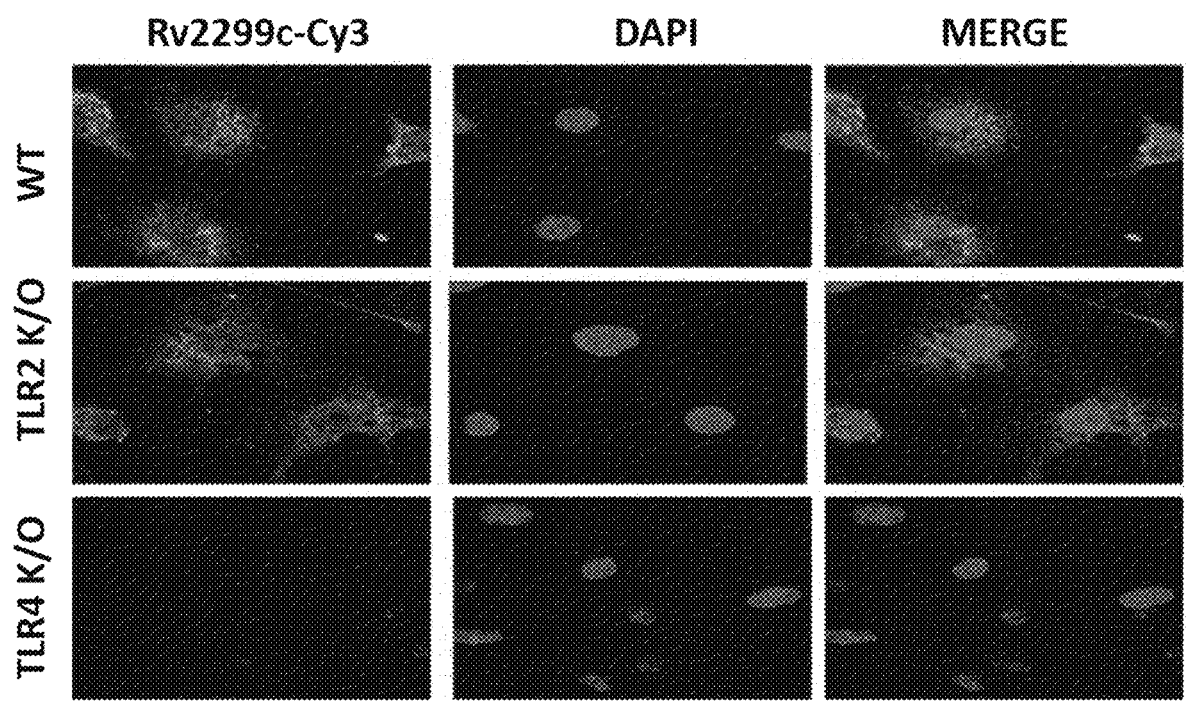
FIGS. 3D, 3E, and 3F are images illustrating confocal microscopy (3D), FACS analysis graph (3E), and binding to TLR4, other than TLR2, to show the interaction of dendritic cells with Rv2299c.
Figure 3E:
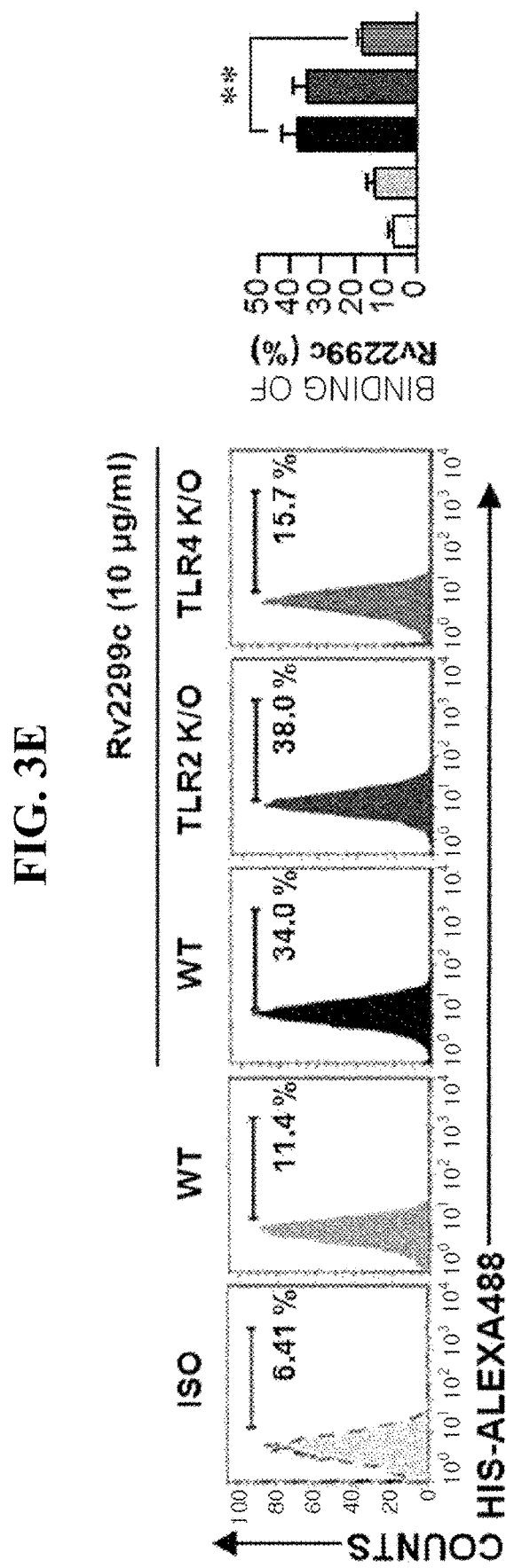
Figure 3F:
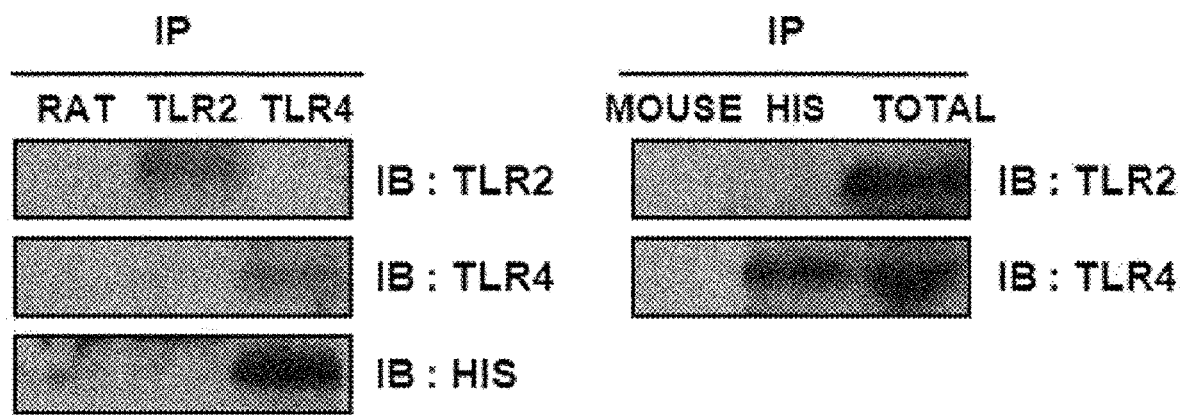

Several Mtb components which activate DCs through a toll-like receptor (TLRs) pathway have been identified (Harding and Boom, 2010). Therefore, it was investigated whether Rv2299c in DCs could be recognized by TLRs and activated through it. Expression of surface molecules (See FIG. 3A) and proinflammatory cytokines (See FIG. 3B) was greatly inhibited in DCs obtained from TLR4$^{-/-}$ mice, as compared to DCs obtained from wild-type (WT) or TLR2$^{-/-}$ mice. This means that Rv2299c can be an activation agent for TLR4. MyD88 is a common adapter molecule for all TLRs, but TRIF is essential for TLR4-mediated activation of the MyD88-independent signaling pathway (Takeda et al., 2003). Determination of the proinflammatory cytokine production in DCs obtained from WT, MyD88$^{-/-}$ and TRIF-deficient mice suggests that MyD88- and TRIF-dependent pathways are involved in the Rv2299c-induced production of TNF-α, IL-6 and IL-1β (See FIG. 3C). Next, it was examined whether Rv2299c interacts with TLR4 molecules in DCs. Confocal microscopy with Cy3-conjugated anti-Rv2299c polyclonal antibodies showed that Rv2299c preferentially binds to the surface of DCs obtained from WT and TLR2$^{-/-}$ other than TLR4$^{-/-}$ DC (See FIG. 3D). Further, binding between Rv2299c and TLR4 molecules was confirmed by FACS analysis (See FIG. 3E). In order to confirm the interaction between Rv2299c and TLR4, the immunoprecipitation assays were performed for anti-TLR2 or anti-TLR4 antibodies and anti-His antibodies. It was found that Rv2299c binds to TLR4 other than TLR2 (See FIG. 3F). These results indicate that Rv2299c induces DC maturation in a TLR4-dependent manner, thereby resulting in increased expression of cell surface molecules and proinflammatory cytokines.

Example 4

MAPK and NF-κB Pathways are Associated with the Maturation of Rv2299c-Mediated Dendritic Cell (DC).

4.1 Experimental Method.

(A) DCs were treated with 10 μg/ml of Rv2299c proteins, and the protein expression was plotted over time. Cell lysates were placed on SDS-PAGE and immunoblot analysis was performed using respective specific antibodies to phospho-p38 (p-p38), p38, phospho-ERK1/2 (p-ERK1/2), phosphor-IκB-a, and p65 NF-κB. (B) Effect of Rv2299c on cellular localization of p65 subunit of NF-κB in DCs. DCs were plated on a closed glass chamber slide and treated with Rv2299c for 1 hour. After the stimulation, the immunoreactivity of p65 subunit of intracellular NF-κB was determined by immunofluorescence as described in "Materials and Methods." (C and D) DCs were treated with p38 (SB203580, 20 μM), ERK1/2 (U0126, 10 μM), JNK (SP600125, 20 μM), Bay11-7082 (20 μM) or DMSO (vehicle control) pharmacological inhibitors for 1 hour before they were treated with 10 μg/ml of Rv2299c proteins for 24 hours. Expression of CD80 and CD86 was analyzed by flow cytometry. The bar graph shows the ratio of respective CD11c+ cells to surface molecules (mean±SEM for three separate experiments). The amounts of TNF-α, IL-6 and IL-1β in the culture medium were measured by ELISA. Mean±SEM is shown for three independent experiments, and statistical significance (*p<0.05, p<0.01 or *p<0.001) appears for the treatment as compared to Rv2299c-treated control.

4.2 Analysis of Experimental Results

Figure 4A:
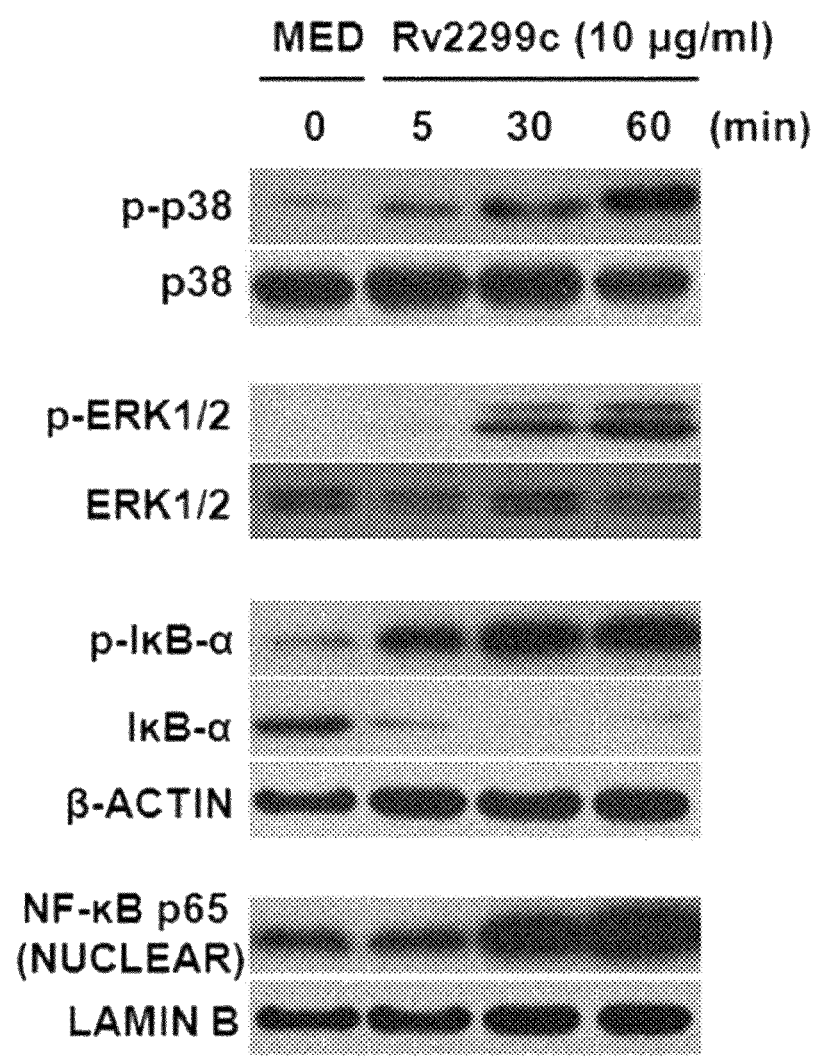
FIG. 4A is a view illustrating the phosphorylation of P38 and ERK 1/2 and the phosphorylation and degradation of IκB-α in DC due to Rv2299c.
Figure 4B:
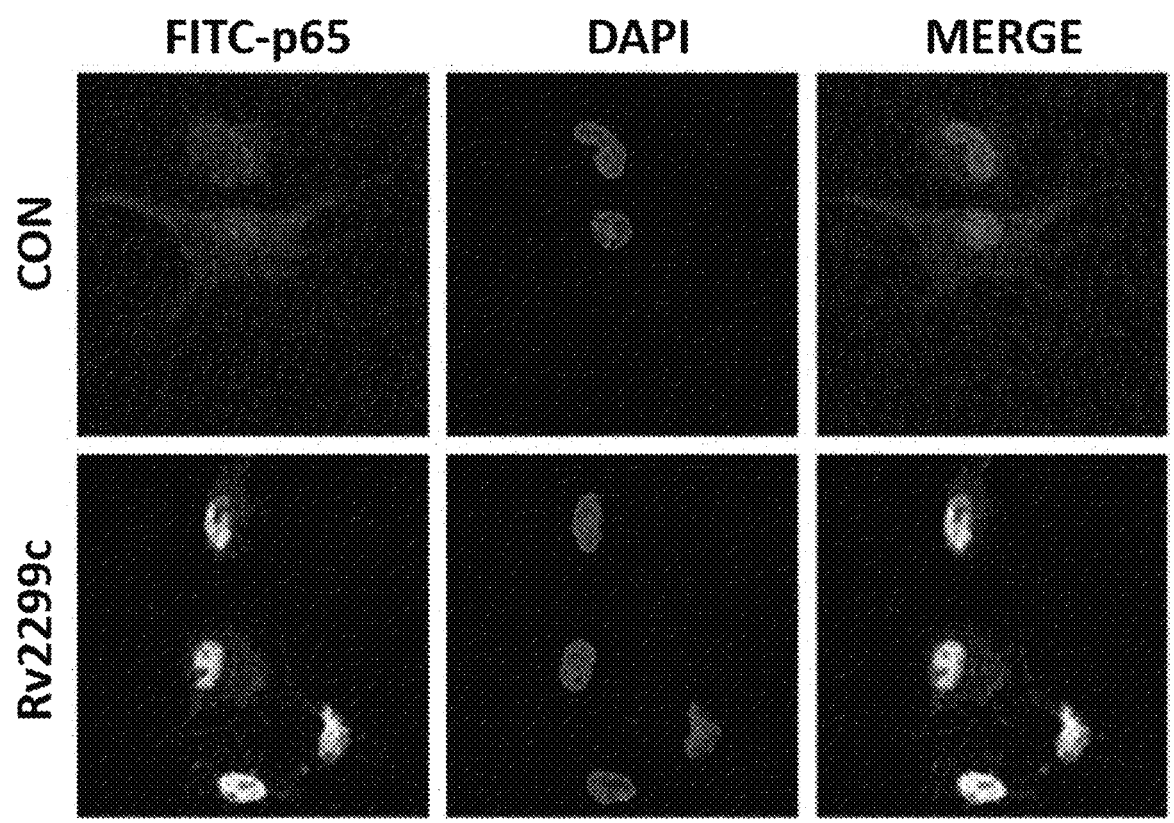
FIG. 4B is a view suggesting the inducement of an important site change from the cytoplasm to the nucleus of p65.
Figure 4C:
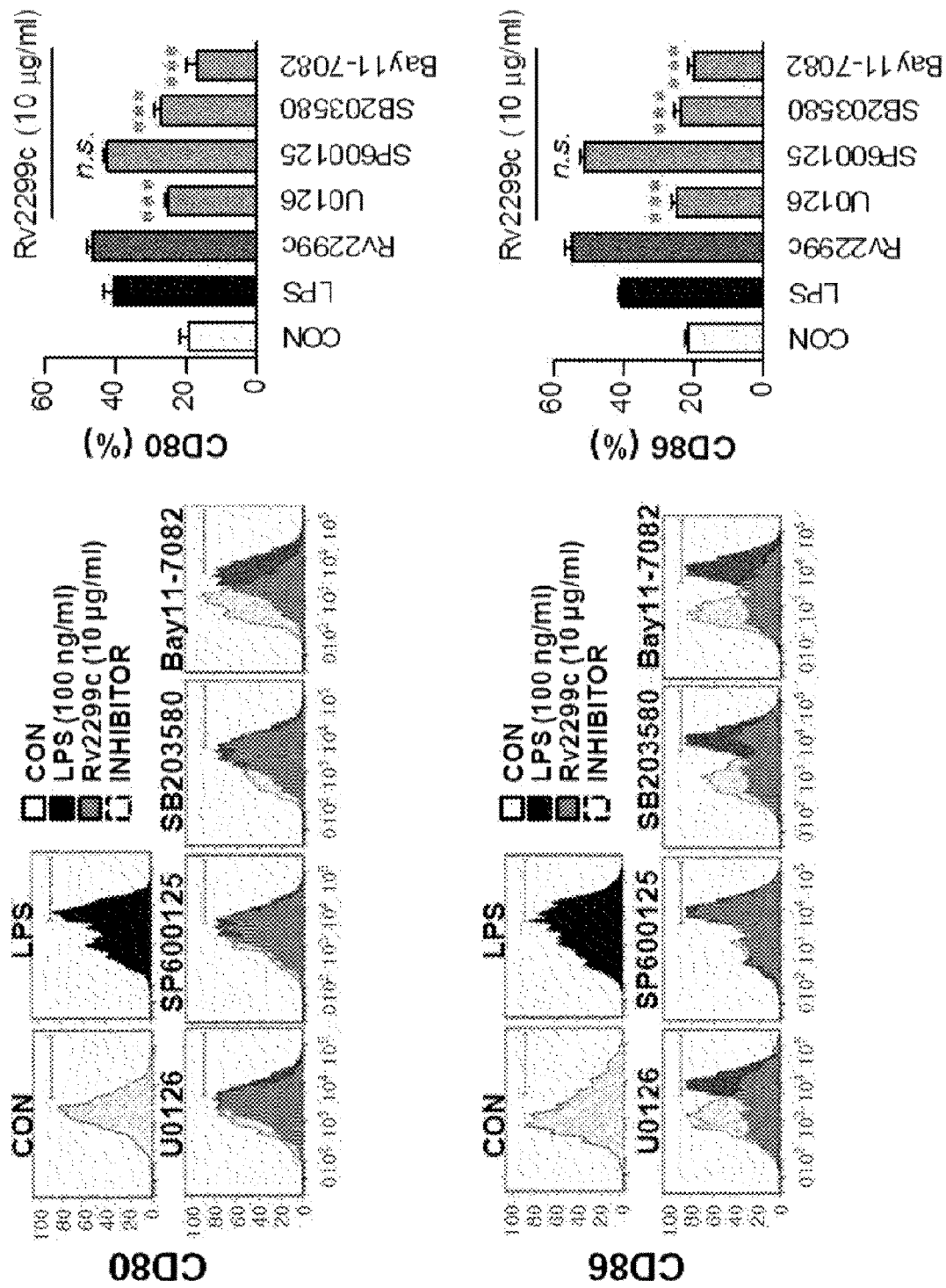
FIGS. 4C and 4D are graphs illustrating that Rv2299c-induced expression (4C) and proinflammatory cytokine production are largely abolished by co-stimulatory molecules on the DC surface by all pharmacological inhibitors except for the JNK inhibitor.
Figure 4D:
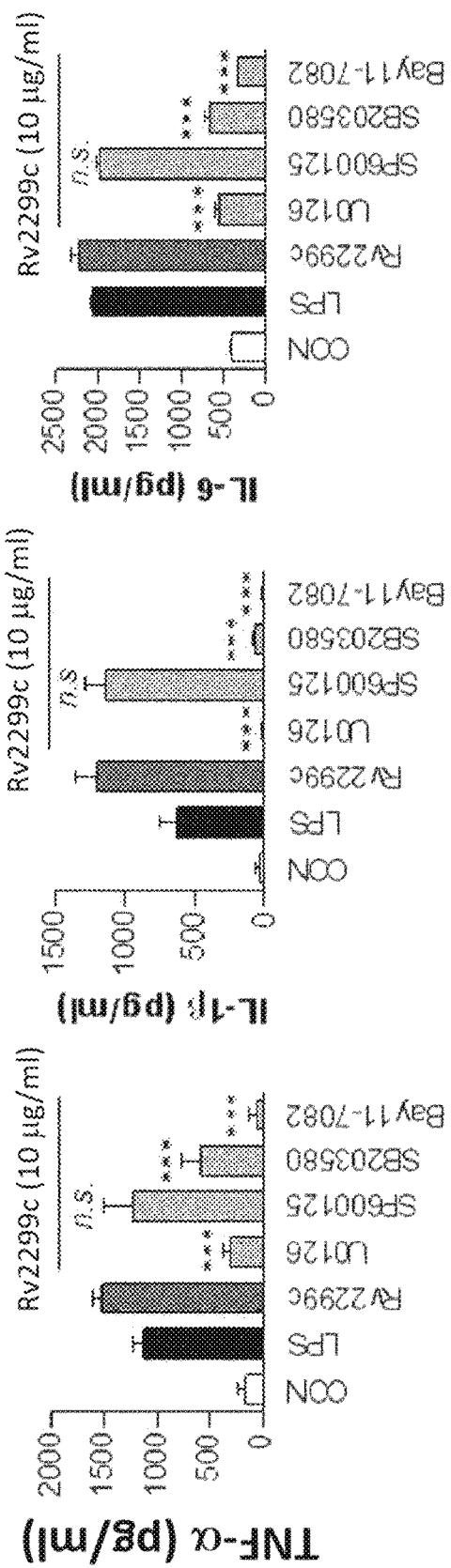

MAPK and NF-κB are critical signaling molecules to regulate DC maturation and proinflammatory cytokine secretion (Bansal et al., 2010b, Pathak et al., 2007). Thus, it was investigated whether MAPK and NF-κB were activated in response to Rv2299c. As expected, Rv2299c caused phosphorylation of p38 and ERK1/2 and phosphorylation and degradation of IκB-α in DCs (See FIG. 4A) and induced a significant site change of p65 from the cytosol to the nucleus (See FIG. 4B). In order to confirm the role of MAPK and NF-κB in Rv2299c-induced proinflammatory cytokine production and co-stimulatory molecule expression, DCs were pre-treated with p38 inhibitor (SB203580), ERK1/2 inhibitor (U0126), JNK inhibitor (SP600125), or NF-κB inhibitor (Bay 11-0782) for 1 hour before they were exposed to Rv2299c. All pharmacological inhibitors except the JNK inhibitor largely abolished Rv2299c-induced expression of co-stimulatory molecules (See FIG. 4C) and proinflammatory cytokine production (See FIG. 4D) on the DC surface. These results reveal that the MAPK and NF-κB signaling pathways are essential for proinflammatory cytokine production and DC maturation marker expression induced by Rv2299c.

Example 5

Rv2299c-Mature Dendritic Cells (DCs) Induce Naive T Cell Proliferation.

5.1 Experimental Method (A) Transformed OVA-specific CD8+T cells and transformed OVA-specific CD4+T cells were isolated and stained with CFSE. They were simultaneously cultured with Rv2299c (10 µg/ml) or LPS (100 ng/ml)-treated DCs for 96 hours. OVA-specific CD8+T cells and OVA-specific CD4+T cells, respectively, were pulsed with OVA25764 (1 µg/ml) and OVA323339 (1 µg/ml). T cells alone and T cells simultaneously-cultured with untreated DCs served as control. OT-I+ and OT-II+ T cell proliferation was evaluated by flow cytometry. (B) Cultured supernatants and IFN-γ, IL-2 and IL-4, harvested after 24 hours therefrom were measured by ELISA. Mean±SEM is shown for three independent experiments, and statistical significance (*$p<0.05$) is shown for the treatment as compared to the appropriate control (T cells/OVA257264-pulsed DCs or T cells/OVA323339-pulsed DCs). n.s refers to treatments without significant effect.

5.2 Analysis of Experimental Results

Figure 5A:
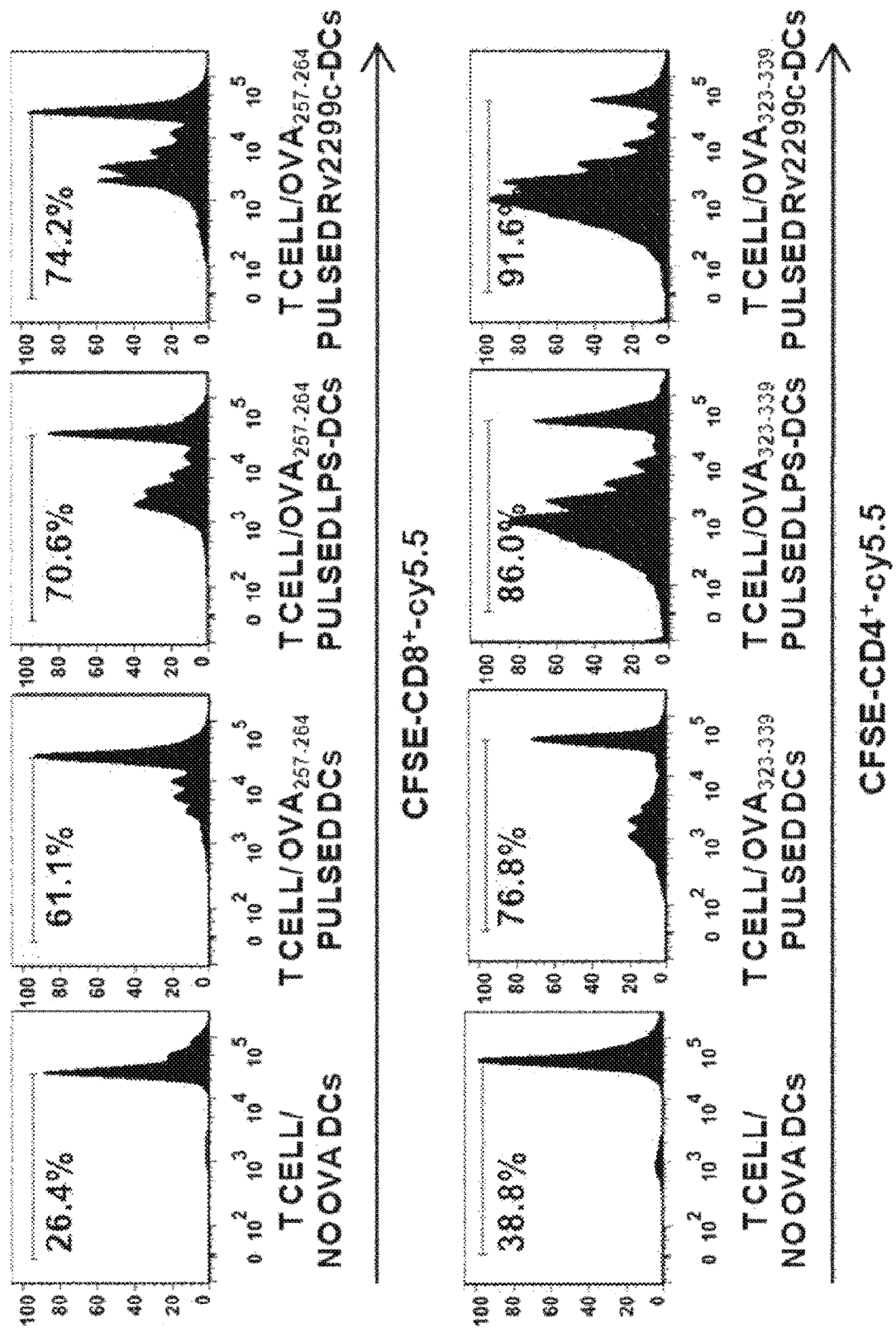
FIGS. 5A and 5B are MLR analysis graphs performed to accurately describe the property of the Rv2299c activity for interaction between DC and T cell, in which FIG. 5A indicates that DC treated with Rv2299c induces T cell proliferation, and FIG. 5B suggests that naive T cell proliferation is induced in the Th1 phenotype.
Figure 5B:
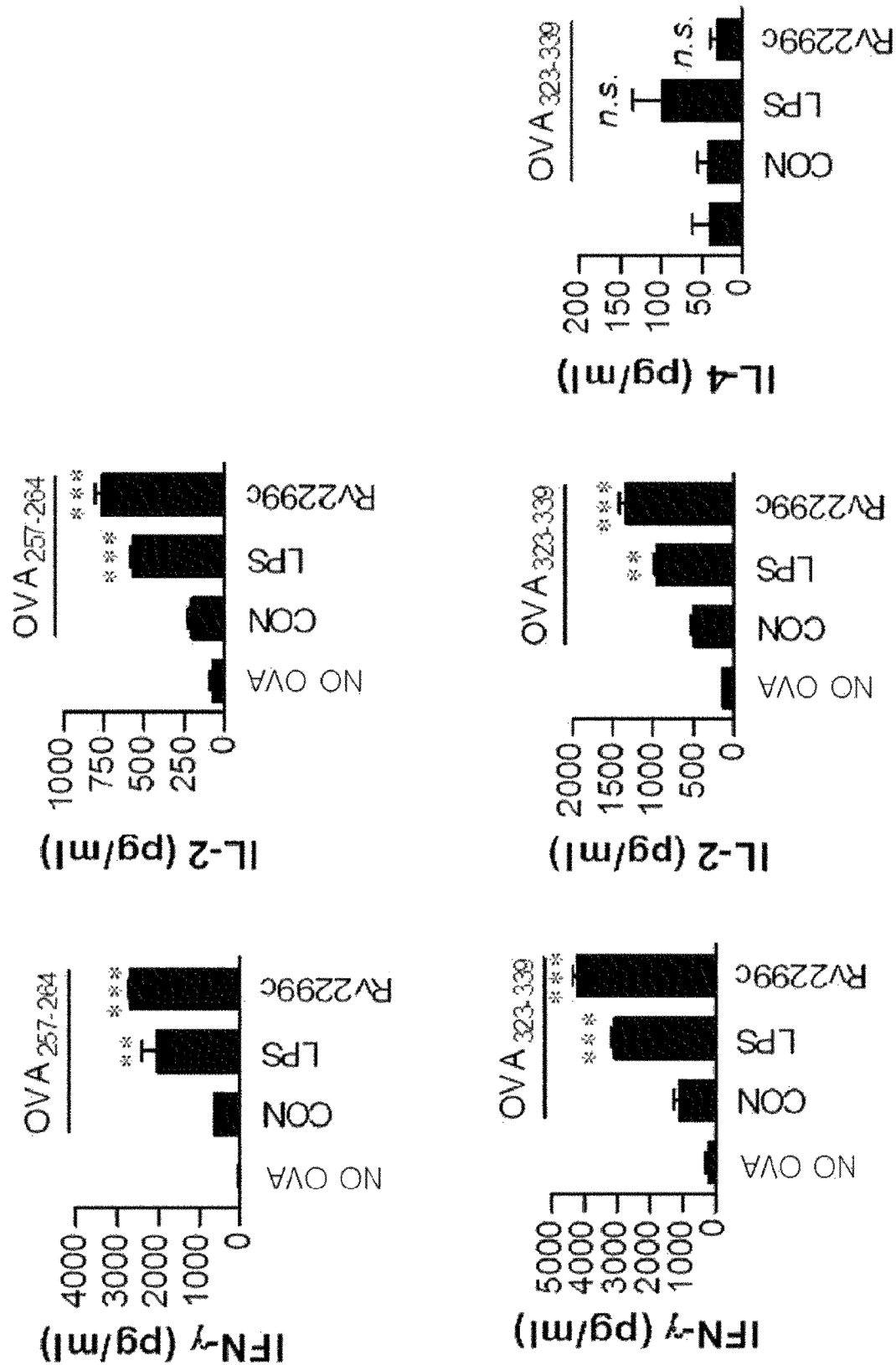

In order to accurately illustrate the property of Rv2299c activity on the interaction between DCs and T cells, syngeneic MLR analysis was performed using OT-I T cell receptor (TCR) transformed CD8+T cells and OT-II TCR transformed CD4+T cells. DCs pulsed with $OVA_{257-264}$ or $OVA_{323-339}$ were co-cultured with transformed CFSE-labeled OVA-specific CD4+ or CD8+ T cells for 72 hours. Rv2299c- or LPS-treated DCs induced T cell proliferation to a significantly greater extent compared to untreated DCs (See FIG. 5A). Further, naive CD4+ and CD8+ T cells pulsed with Rv2299c-treated DCs were produced at much higher IFN-γ and IL-2 levels compared to untreated DCs ($p<0.05$-$0.01$), whereas IL-4 secretion was not increased regardless of Rv2299c stimulation (See FIG. 5B). These results suggest that Rv2299c-treated DCs induce naive T cell proliferation to a Th1 phenotype.

Example 6

Rv2299c-Mature Dendritic Cells (DCs) Induced an Expansion of Effect/Memory T Cell Populations.

6.1 Experimental Method (A) T cells prepared from *Mycobacterium tuberculosis*-infected BALB/c mice. DCs were cultured with 10 µg/ml of Rv2299c proteins for 24 hours. Rv2299c-mature DCs were washed and co-cultured with allogeneic T cells at DCs to T cells ratio of 1:10 for 3 days. Splenocytes were stained with anti-CD4, anti-CD8 mAb, anti-CD62L and anti-CD44 mAb. The bar graph show $CD62L^{low}CD44^{high}$T cells in the spleen. The bar graph shows the ratio (mean±SEM) for CD4+/CD8+CD44$^{high}$ and CD4+/CD8+CD62L$^{low}$ T cells in three independent experiments. (B) Expression of IFN-γ, IL-2 or IL-4 in CD3+/CD4+ and CD3+/CD8+ cells was analyzed in T cells of intestinal lymph nodes co-cultured with Rv2299c-pulsed DCs or LPS-pulsed DCs by intracellular IFN-γ, IL-2 or IL-4 staining. The proportion of double-positive cells in T cells is shown in the upper right corner, and the results represent three independent experiments. Statistical significance ($p<0.01$ or *$p<0.001$) is shown for comparison as compared to untreated DC, and n.s refers to no significant effect.

6.2 Analysis of Experimental Results

Figure 6A:
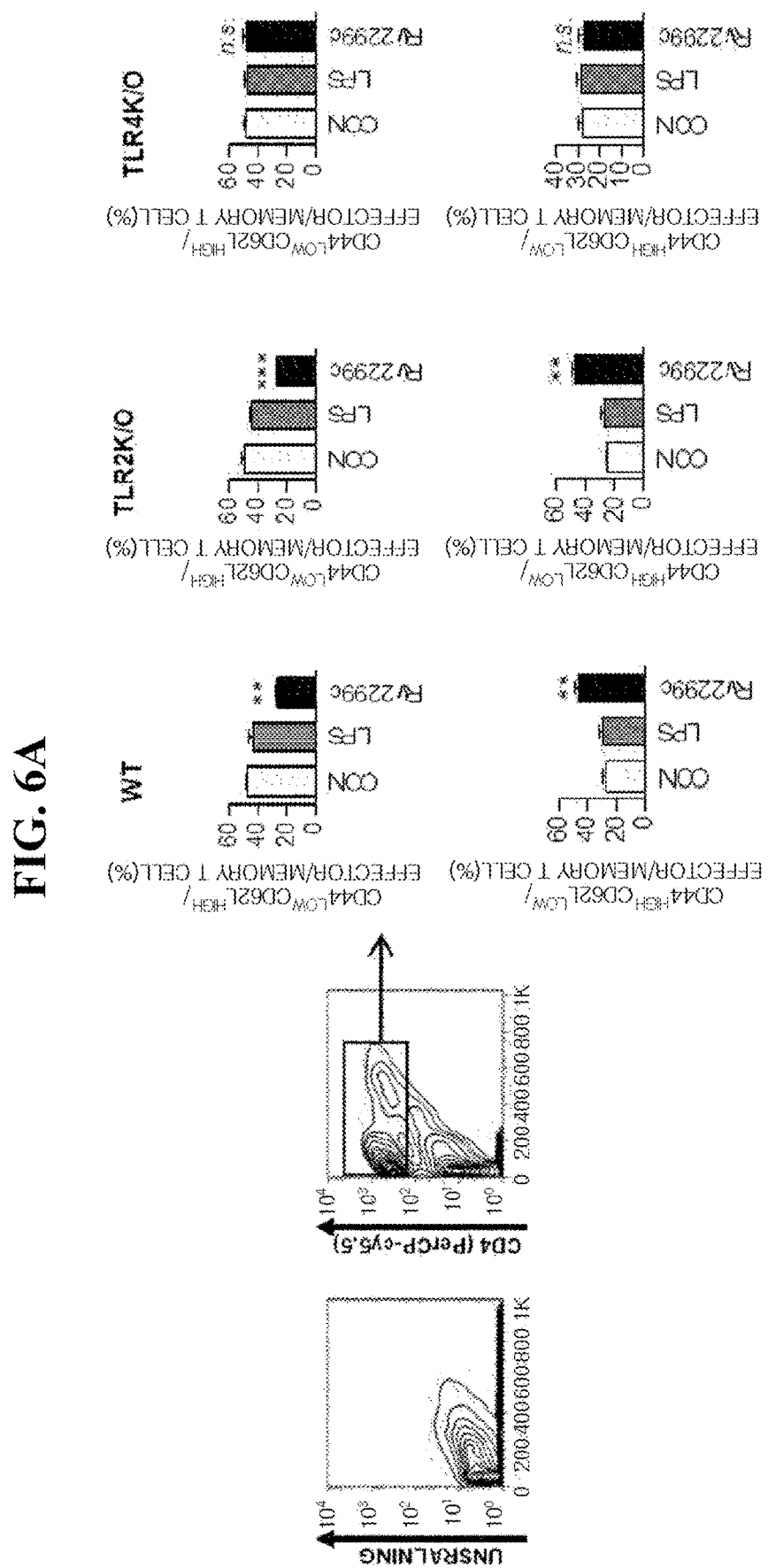

In order to assess whether Rv2299c-stimulated DCs were reflected in their ability to particularly stimulate CD4+ obtained from mice infected with Mtb, the flow cytometry was used to analyze a change in expression of CD62L and CD44 in CD4+ splenic T cells induced Rv2299c-treated DCs. DCs were prepared from the bone marrow of WT, TLR2$^{-/-}$ or TLR4$^{-/-}$ mice and matured with Rv2299c or LPS. Both Rv2299c-mature DCs obtained from infected mice and syngenic CD4+ T cells were co-cultured for 72 hours. Then, Rv2299c-mature DCs obtained from WT or TLR2$^{-/-}$ mice, other than TLR4$^{-/-}$ mice, showed down-regulated CD62L and up-regulated CD44 expression in CD4+ T cells compared to control DCs or LPS-treated DCs (See FIG. 6A). The proportion of CD4-IFN-γ or CD4-IL-2 positive cells was significantly higher in the co-culture with Rv2299c-mature DCs obtained from WT or TLR2$^{-/-}$ mice, other than TLR4$^{-/-}$ mice compared to control DCs or LPS-treated DCs (See FIG. 6B). Further, CD4-IL-4 positive cells did not increase due to the co-culture with antigen-stimulated DCs. These data suggest that Rv2299c-mature DCs induce expansion of effect/memory T cells and drive the Th1 immune response in a TLR4-dependent manner Example 7

T Cells Activated by Rv2299c-Mature Dendritic Cells (DCs) Inhibit Mtb Growth in Cells.

7.1 Experimental Method

BMDM was infected with H37Rv (MOI=1) for 4 hours. The infected BMDM was then treated with amikacin (200 µg/ml) for 2 hours and washed twice with PBS. Then, the previously prepared mixture was added to each shell of the plate and was cultured for 3 days. The mixture was antigen-activated DCs which were co-cultured with CD4+ T cells at a DC to T cell ratio of 1:10 for 3 days. The DCs activated the antigen were LPS (100 ng/ml) and Rv2299c (10 µg/ml). (A) Number of Mtb in infected macrophages. (B) The supernatant was analyzed using ELISA. The data shown is mean value±SD (n=3); *$p<0.05$, $p<0.01$ or *$p<0.001$ refers to a significance for treated cells versus untreated cells. Treatments without significant effects are denoted by n. s.

Figure 7:
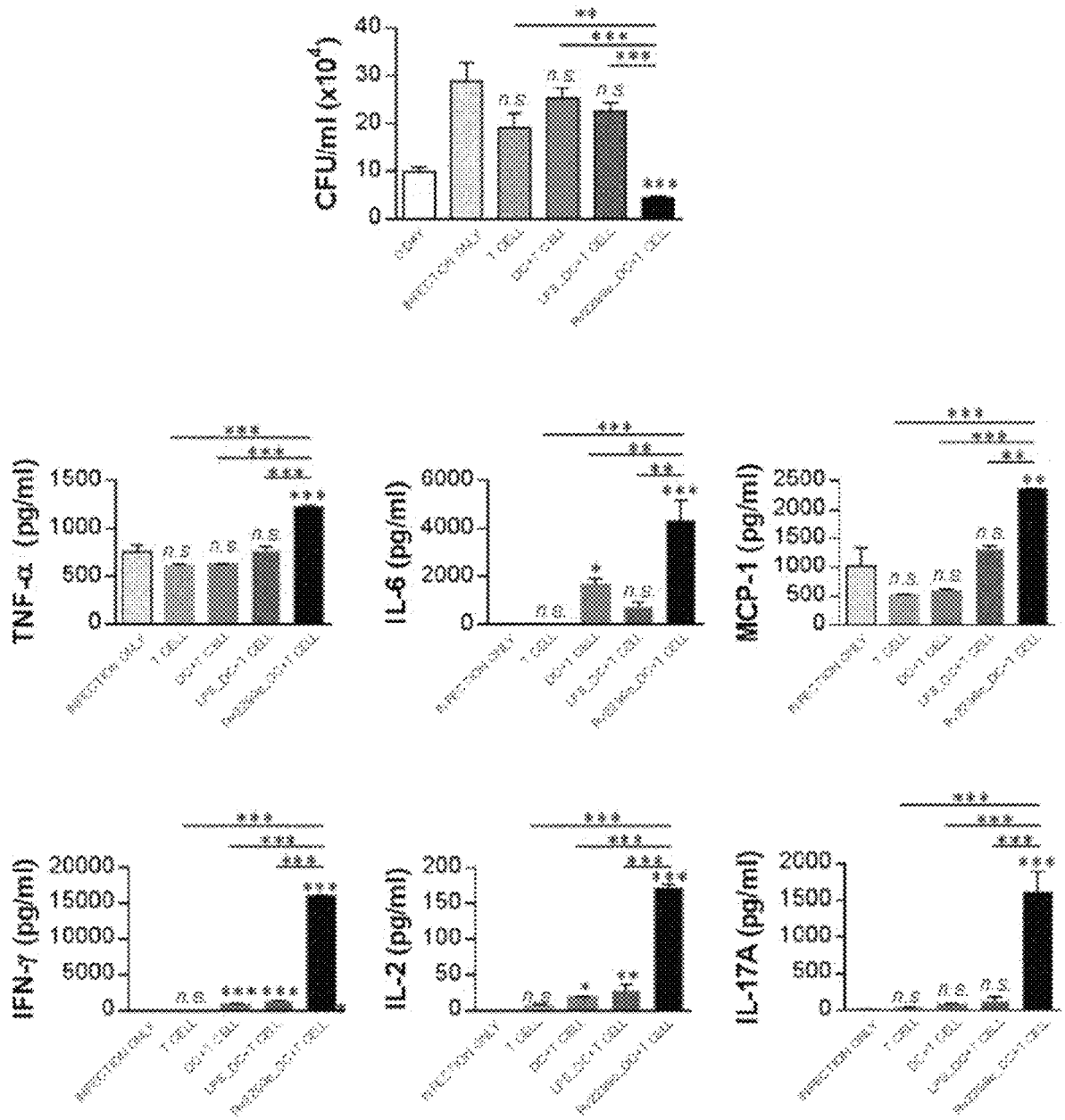
FIG. 7 is a graph illustrating that Rv2299c inhibits Mtb growth and induces the activity of T cells having bactericidal activity through DC maturation.

7.2 Analysis of Experimental Results In order to confirm that Rv2299c-mature DCs actually play a role in controlling Mtb, it was investigated whether T cells activated by Rv2299c-mature DCs could enhance bactericidal action in macrophages. Naive spleen T cells from uninfected mice were activated by co-culturing with Rv2299c-mature DCs for 72 hours and then added to the Mtb-infected BMDM. As illustrated in FIG. 7A, the simple addition of inactivated T cells significantly inhibited Mtb growth in the cells. Interestingly, Mtb growth was significantly inhibited by treating T cells activated by Rv2229c-stimulated DCs compared to inactivated T cells or T cells activated by LPS-stimulated DCs. The proinflammatory cytokines, IFN-γ and IL-17 associated with anti-tuberculosis activity were significantly increased when T cells activated by Rv2299c-stimulated DCs were added thereto, compared to inactivated T cells or T cells activated by LPS-stimulated DCs. The results indicate that the inhibition of Mtb growth is associated with this cytokine production (See FIG. 7B). These results suggest that Rv2299c induces activation of T cells with bactericidal activity through DC maturation.

Example 8

Fusion Protein of Rv2299c and ESAT-6 Enhances the Immune Response of ESAT-6.

8.1 Experimental Methods to Confirm that Fusion Proteins Induce Dendritic Cell (DC) Maturation (A) BMDCs were cultured for 24 hours in the presence of 1, 2, 5, 10 or 20 µg/ml of ESAT-6 or fusion proteins and analyzed by flow cytometry. Staurosporine was a positive control. DCs were stained with anti-CD11c, Annexin V and PI. The proportion of positive cells (annexin V- and PI-stained cells) in each quadrant is shown. The results represent three experiments. (B) BMDCs were cultured in the presence of 1, 5 or 10 μg/ml of fusion proteins, 2 μg/ml of ESAT-6 or 10 μg/ml of Rv2299c for 24 hours and analyzed by two-color flow cytometry. The cells were gated to exclude CD11c cells. DCs were stained with anti-CD40, anti-CD80, anti-CD86 or anti-MHC class II. The results represent three experimental results. The average fluorescence intensity was calculated from the above graph. Each bar represents the average fluorescence level of the sample. Data are presented as means±SEM (n=5). *p<0.05, p<0.01 and *p<0.001 as compared to the untreated control, ESAT-6, or Rv2299c. (C) The supernatant was measured by ELISA. The results come from one representative experiment of the three experiments conducted. Data are presented as means±SEM (n=5). *p<0.05, p<0.01 and *p<0.001 as compared to the untreated control, ESAT-6, or Rv2299c.

8.2 Experimental Method to Confirm Inhibition of Mtb Growth in Macrophages by Fusion Proteins BMDM was infected with H37Rv (MOI=1) for 4 hours. The infected BMDM was then treated with amikacin (200 μg/ml) for 2 hours and washed twice with PBS. Then, the previously prepared mixture was added to each shell of the plate and was cultured for 3 days. The mixture was antigen-activated DCs which were co-cultured with CD4+ T cells at a DC to T cell ratio of 1:10 for 3 days. The DCs that activated the antigen were ESAT-6 (2 μg/ml), Rv2299c, and fusion protein (10 μg/ml). (A) Number of Mtb in infected macrophages. (B) The supernatant was analyzed using ELISA. The data shown is mean value±SD (n=3); *p<0.05, p<0.01 or *p<0.001 refers to a significance for treated cells versus untreated cells. Treatments without significant effects are denoted by n. s.

8.3 Analysis of Experimental Results

Figure 8A:
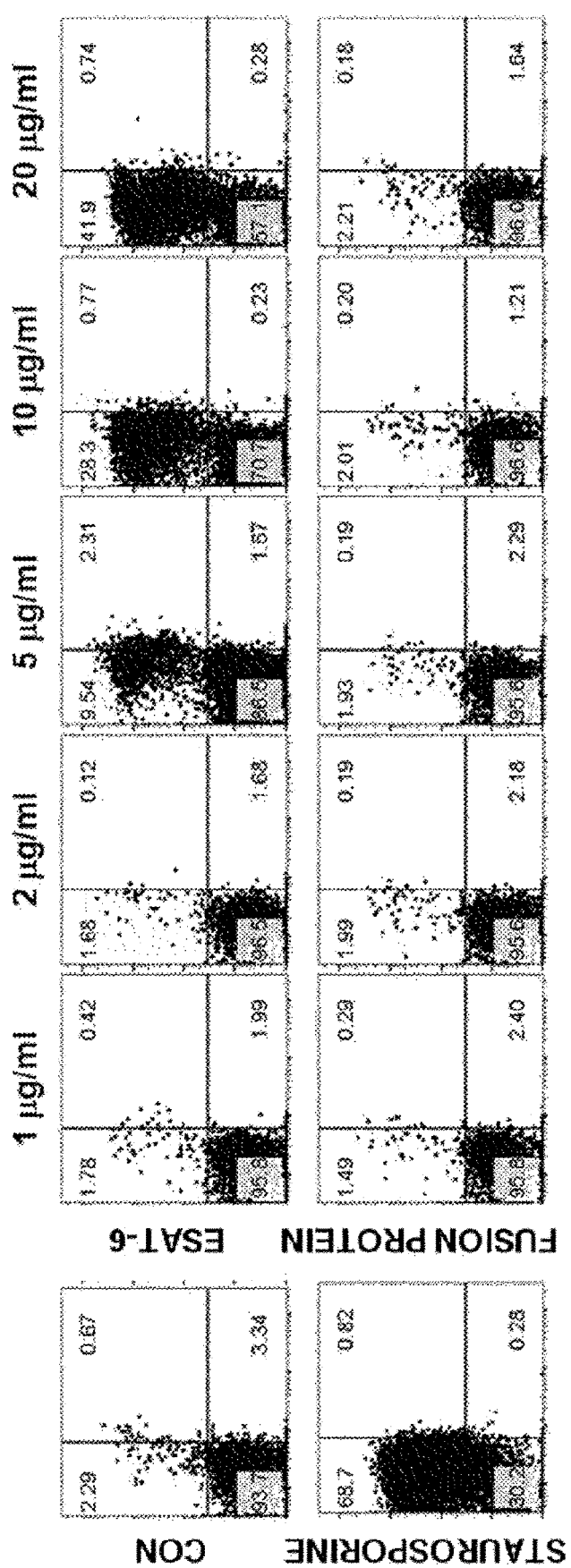
FIG. 8A is a view illustrating cytotoxicity of the recombinant fusion protein of Rv2299c and ESAT-6.
Figure 8B:
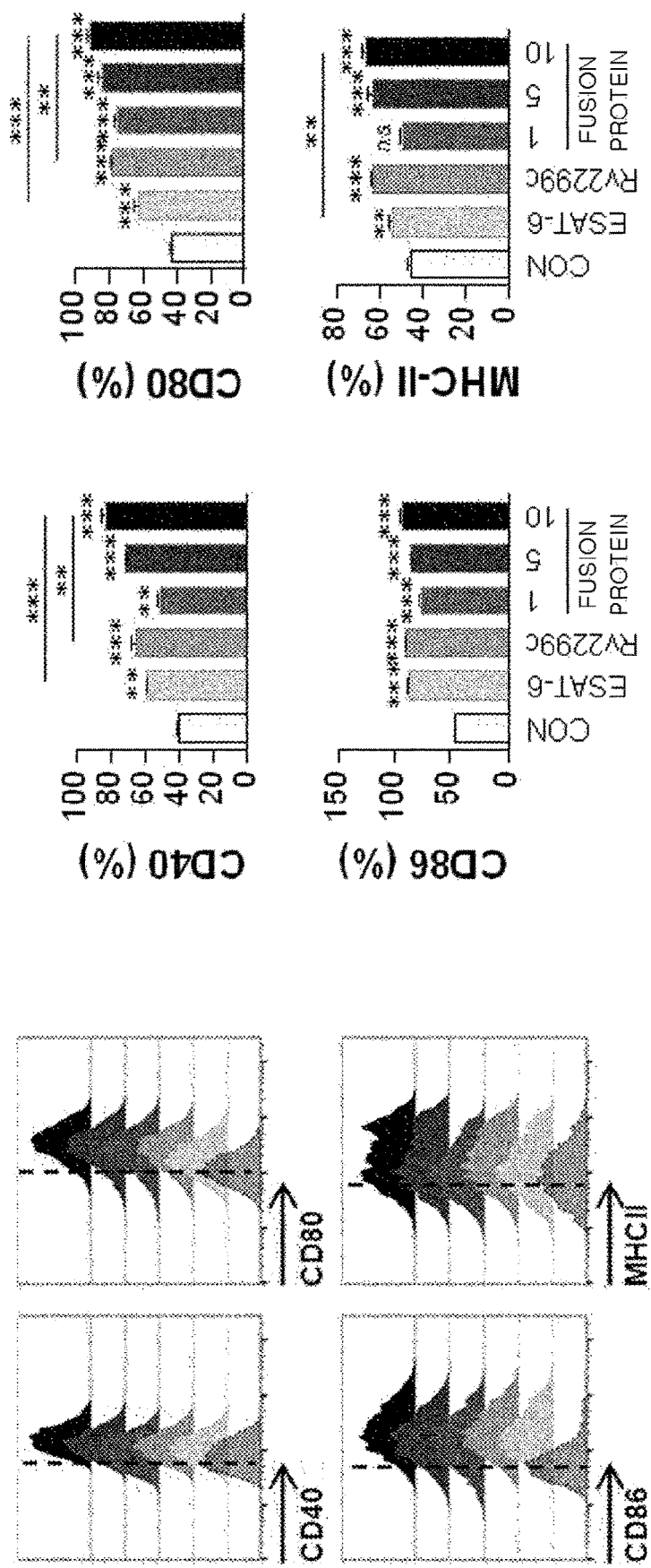
FIGS. 8B and 8C are graphs illustrating the expression of MHC molecules and the expression of proinflammatory cytokines such as TNF-α, IL-12 and IL-1β in the recombinant fusion protein of Rv2299c and ESAT-6.
Figure 8C:
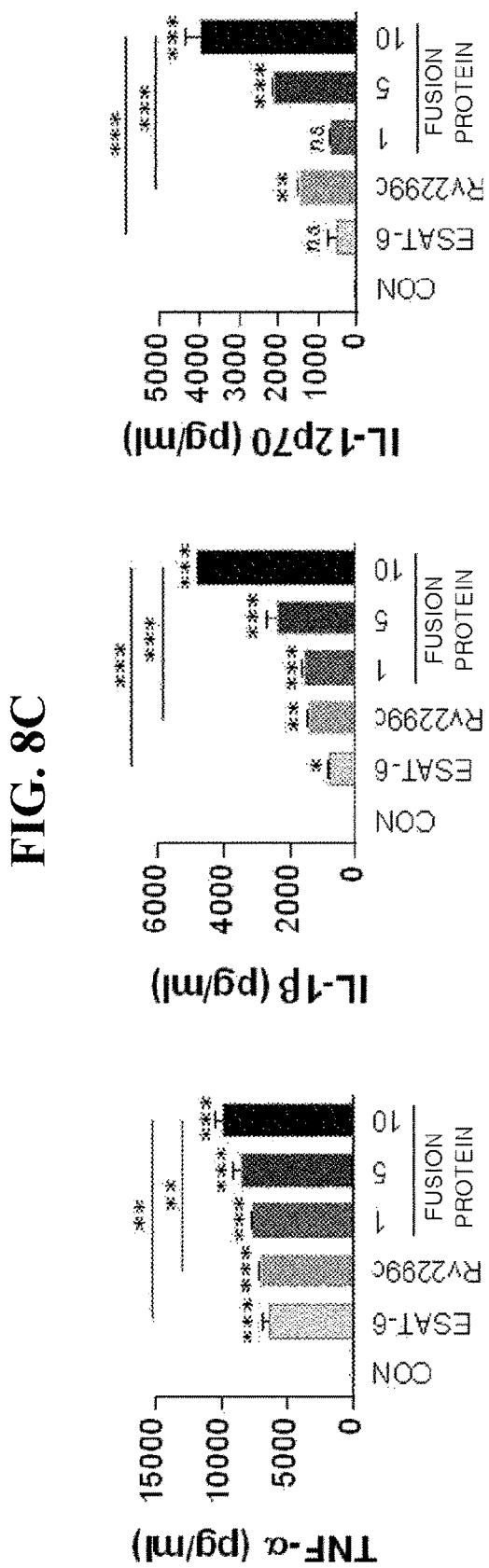
Figure 9A:
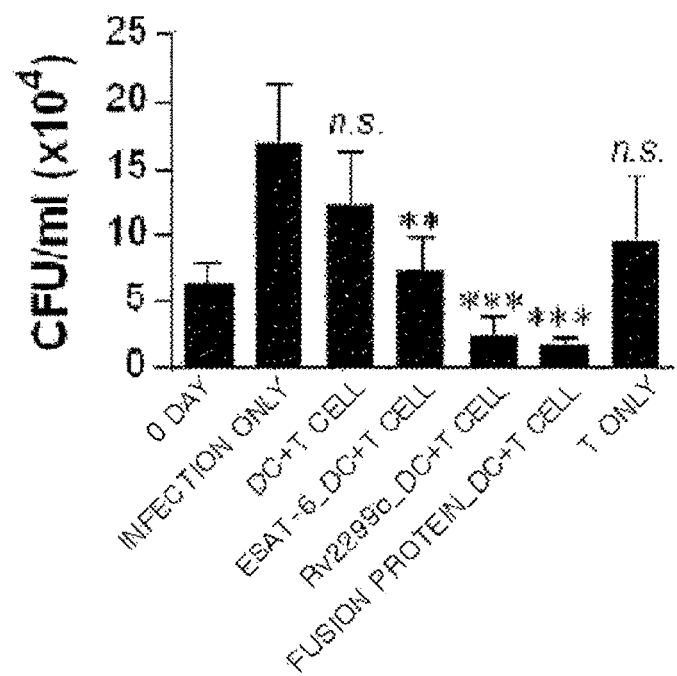
FIG. 9A is a graph illustrating that Mtb growth was significantly inhibited by the addition of T cells activated with ESTA-6-stimulated DC.
Figure 9B:
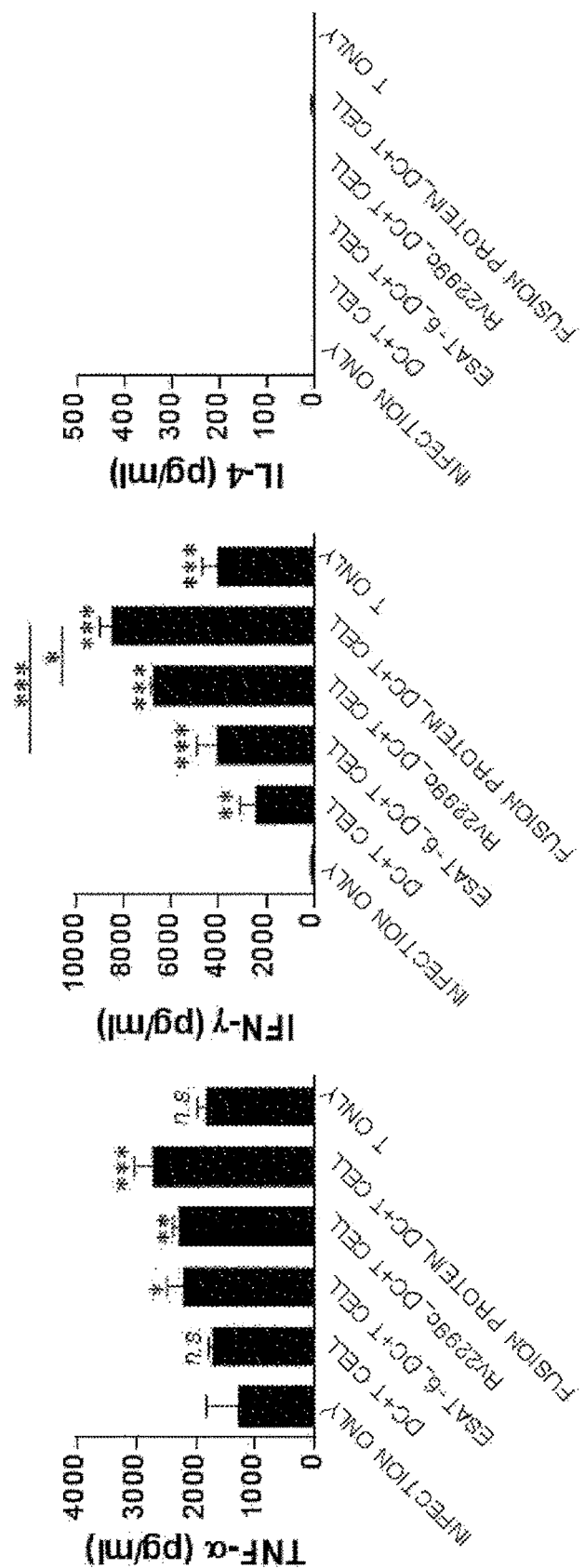
FIG. 9B is a graph illustrating that high production of proinflammatory cytokines such as IFN-γ and TNF-α is caused when Mtb-infected BMDM co-cultures with T cell activated by fusion protein-stimulated DC.

It was assumed that DC-activated proteins could enhance the prophylactic immunity of T cell-stimulating antigens. In order to test this assumption, ESAT-6, a major T cell vaccine candidate, was expressed and purified in proteins fused to Rv2299c in *E. coli*, and its immunogenicity was investigated. First, the cytotoxicity of recombinant Rv2299c-fused ESAT-6 in BMDM was determined by annexin V and propidium iodide (PI) staining. ESAT-6 showed cytotoxicity higher than 5 μg/ml, but the fusion proteins did not show toxicity at 10 μg/ml (See FIG. 8A). Thus, ESAT-6 was used at a concentration of 2 μg/ml in subsequent experiments. The co-stimulation, the expression of MHC molecules, and the production of proinflammatory cytokines such as TNF-α, IL-1β and IL-12 increased significantly in DCs stimulated with fusion proteins as compared to a single protein (See FIG. 8B). Next, the bactericidal activity of the T cells stimulated by the fusion protein-mature DCs was determined. As illustrated in FIG. 9A, intracellular Mtb growth was significantly inhibited by the addition of T cells activated with ESAT-6-stimulated DCs compared to BMDM cells without any T cells or DCs, but T cells activated by stimulated by Rv2299c-stimulated DCs or fusion protein-stimulated DCs significantly inhibited intracellular Mtb growth compared to other conditions. High production of proinflammatory cytokines such as IFN-γ and TNF-α was shown when Mtb-infected BMDM was co-cultured with T cells activated by fusion protein-stimulated DCs (See FIG. 9B).

Example 9

Fusion Proteins of Rv2299c and ESAT-6 Elicit a Significant BCG Prime Boosting Effect on the Highly Virulent Strain Mtb HN878 Strain.

9.1 Experimental Method (A) Vaccination schedule and experimental design, (B) The difference in the degree of bacterial growth in one mouse lung is shown in the lung of the mice vaccinated with BCG alone, protein alone, BCG/Rv2299c+ESAT-6 fusion protein and adjuvant control (MPL-DDA only) at 16 weeks after challenge with Mtb HN878. (C) The lung sections from each mouse vaccinated at 16 weeks after challenge with Mtb HN878 (n=6 animals/group) were stained with H&E (D) Percentage of inflammatory tissue sites in lung tissue sections. G1: infection control, G2: MPL/DDA inoculation control, G3: BCG alone, G4: BCG/Rv2299c+ESAT-6/MPL-DDA fusion protein inoculation, G5: ESAT-6/MPL-DDA inoculation group. *P<0.05, p<0.01 and *p<0.001 compared to the MPL-DDA-alone group.

9.2 Analysis of Experimental Results

Finally, it was assessed whether the Rv2299c+ESAT-6 fusion protein is potentially a vaccine against TB. First, Mtb Erdman strain was used to evaluate the vaccine effect of Rv2299c protein alone in a mouse model. However, in views of reducing bacterial burden in the lungs and spleen, the Rv2299c/MPL-DDA inoculation did not show a significant protective effect on the Erdman strain.

Figure 10A:
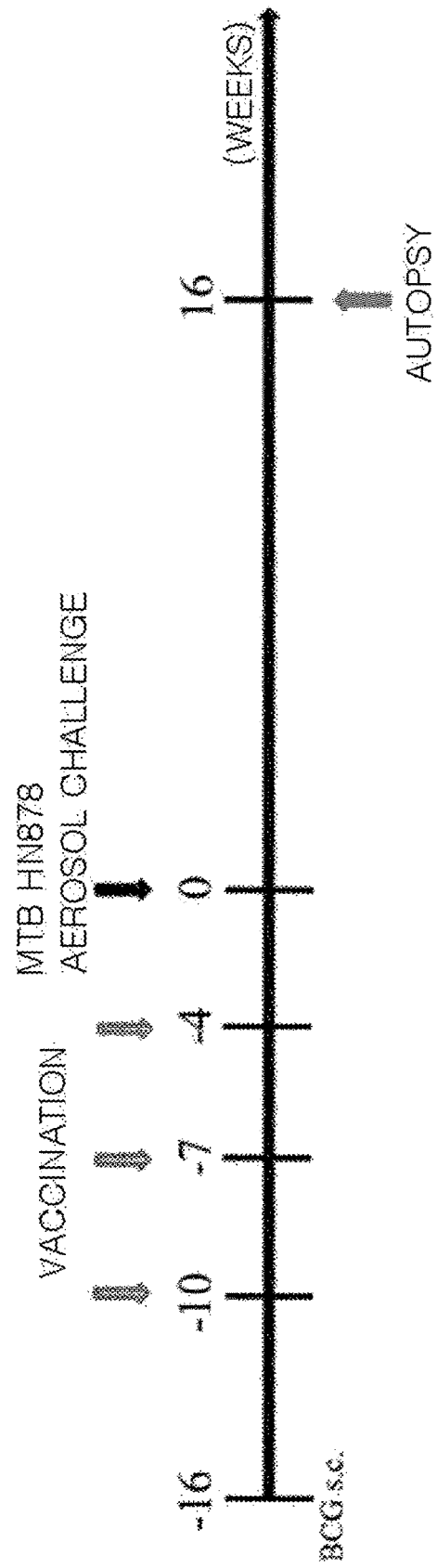
FIG. 10A is a schematic diagram illustrating BCG prime boosting effect on a highly virulent HN878 strain by a fusion protein of Rv2299c and ESAT-6.
Figure 10B:
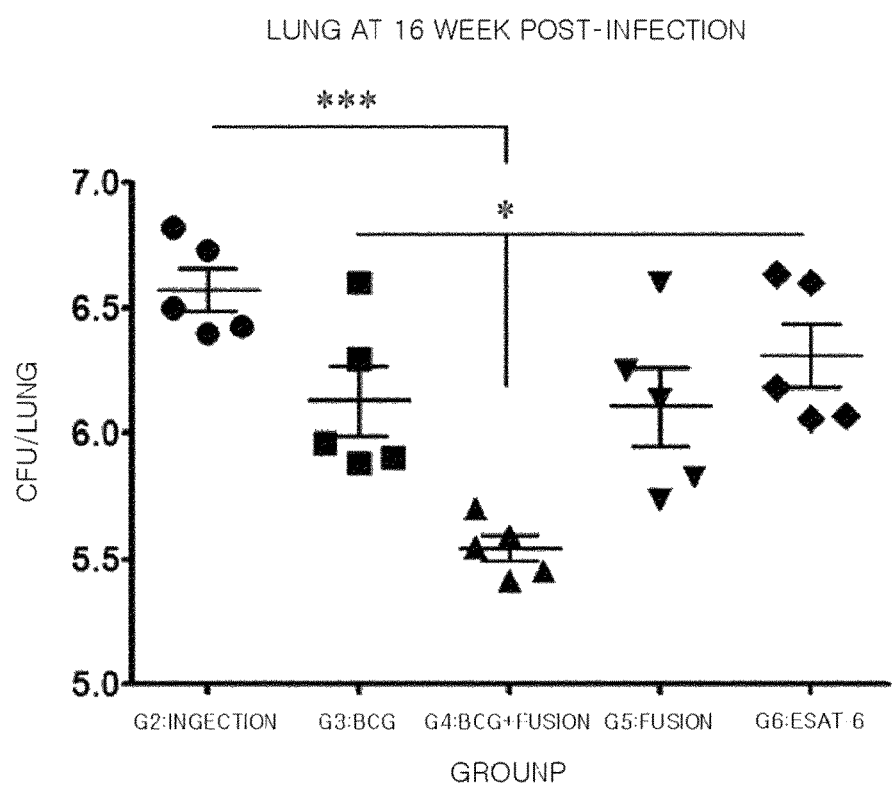
FIG. 10B is a graph illustrating that all BCG alone, ESAT-6 fusion protein and Rv2299c+ESAT fusion protein decreased bacterial load in the lungs.
Figure 10C:
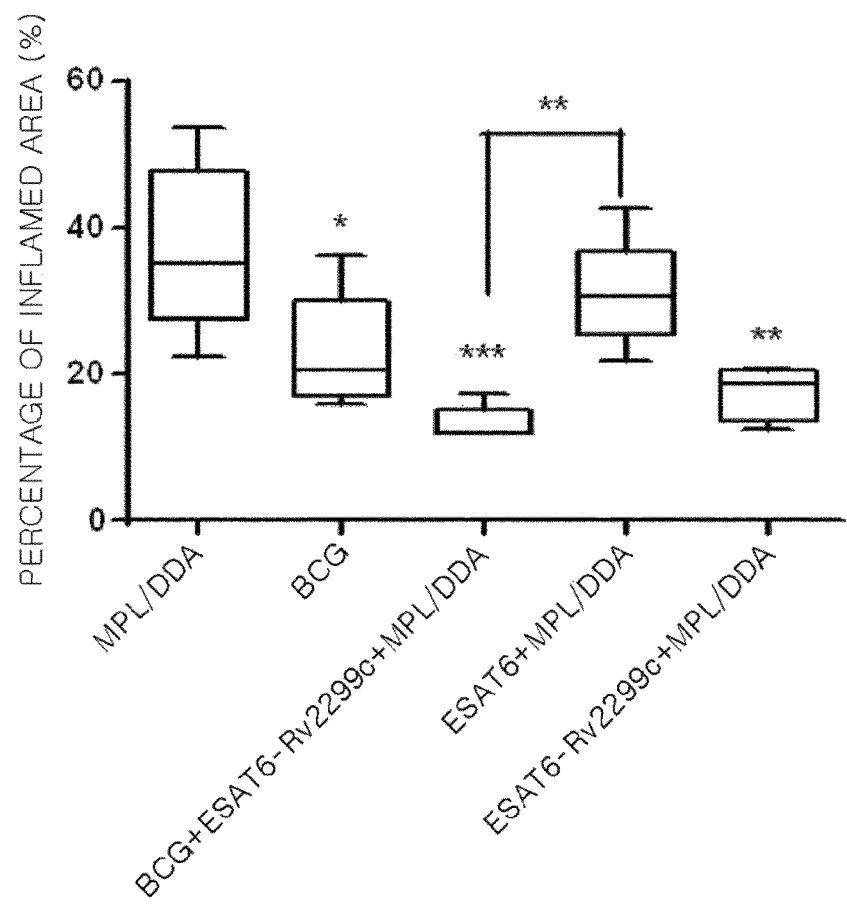
FIGS. 10C and 10D are graphs illustrating the preventive effect of the fusion protein of Rv2299c and ESAT-6 against the HN878 strain challenge from the viewpoint of a long-term bacterial reduction.
Figure 10D:
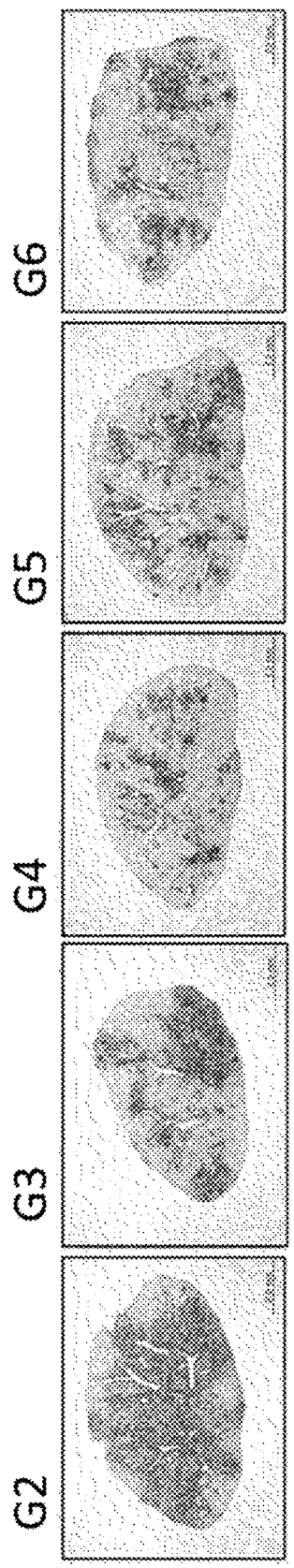

Next, it was assessed whether the Rv2299c+ESAT-6 fusion protein is potentially a BCG-prime booster in the challenge model of Mtb HN878, the highly pathogenic *M. tuberculosis* strain. Previous studies have shown that BCG-only vaccination of mice provides less protection against W-Beijing isolates compared to Mtb H37Rv at 10 weeks after post-infection (Lopez et al., 2003). Thus, as described above, the vaccine efficacy of the protein in the mouse model was tested using a clinically highly virulent HN878 strain, one of the W-Beijing families (Cha et al., 2015b). Four weeks after the final vaccination, mice were challenged with the Mtb HN878 strain, and bacterial load in their lungs was determined at 16 weeks (See FIG. 10A). As illustrated in FIG. 10B, all BCG alone, ESAT-6 and Rv2299c+ESAT-6 fusion proteins significantly reduced bacterial load in the lungs compared to the adjuvant control group. The BCG alone and fusion proteins showed similar preventive effects, and ESAT-6 vaccination showed higher bacterial load in the lungs. However, these three vaccines did not show much difference one another. In order to boost the BCG vaccine, the ability of the fusion protein was also examined 16 weeks after infection, fusion protein-boost mice showed significantly lower numbers of bacteria compared to BCG-vaccine mice. The lung inflammation was also evaluated after the vaccination. At 16 weeks after the challenge, the Rv2299c+ESAT-6 fusion protein-vaccinated group showed significantly reduced pulmonary inflammation compared to the BCG control (p<0.01). Overall, the Rv2299c+ESAT-6 fusion protein showed a prophylactic effect against the HN878 strain challenge in views of a long-term bacterial reduction. In addition, at the 16 weeks after the challenge, the Rv2299c+ESAT-6 fusion protein-vaccinated group showed significantly reduced pulmonary inflammation compared to the infected control (p<0.01) (See FIGS. 10C and 10D).

Example 10

Immunogenicity of Antigen-Specific Th1 Immune Responses in Mice Infected with Mtb HN878

10.1 Experimental Method to Confirm the Induction of Antigen-Specific Multifunctional T Cells in the Mouse Lung with Immunity Each group of mice was vaccinated and sacrificed as described in Materials and Methods. 4 weeks after the final vaccination, each group of mice (n=6) was euthanized and their lung cells were stimulated with the labeled antigen in the presence of GolgiStop at 37° C. for 12 hours. The proportion of antigen-specific CD4+ T cells producing IFN-γ, TNF-α, and/or IL-2 in cells isolated from lungs of vaccinated mice was analyzed using multicolor flow cytometry while gating against CD4+ lymphocytes. The pie chart represents the average number of cells co-expressing IFN-γ, TNF-α and/or IL-2. The data were expressed as mean±SD obtained from 5 mice in each group, and independent sample t-test was used to determine a significance. *P<0.05, p<0.01 and *p<0.001 as compared to the MPL-DDA-alone group (independent sample t-test).

10.2 Experimental Method to Confirm Maintenance of Multifunctional T Cells in the Spleen after Challenge with *Mycobacterium tuberculosis* Strain HN878.

After 16 weeks of infection, each group of mice (n=6) was euthanized, and their spleen cells ($2.0 \times 10^6$ cells) were stimulated with each antigen (5 µg/ml) in the presence of GolgiStop at 37° C. for 12 hours. The proportion of antigen-specific CD4+ T cells producing IFN-γ, TNF-α, and/or IL-2 in cells isolated from the lung of each group of mice was analyzed using multicolor flow cytometry while gating against CD4+ lymphocytes. The pie chart represents the average number of cells co-expressing IFN-γ, TNF-α and/or IL-2. The data were expressed as mean±SD obtained from 5 mice in each group, and independent sample t-test was used to determine a significance. *p<0.05, p<0.01 and *p<0.001 as compared to the MPL-DDA-alone group (independent sample t-test).

10.3 Analysis of the Aforementioned Experimental Results

Figure 11A:
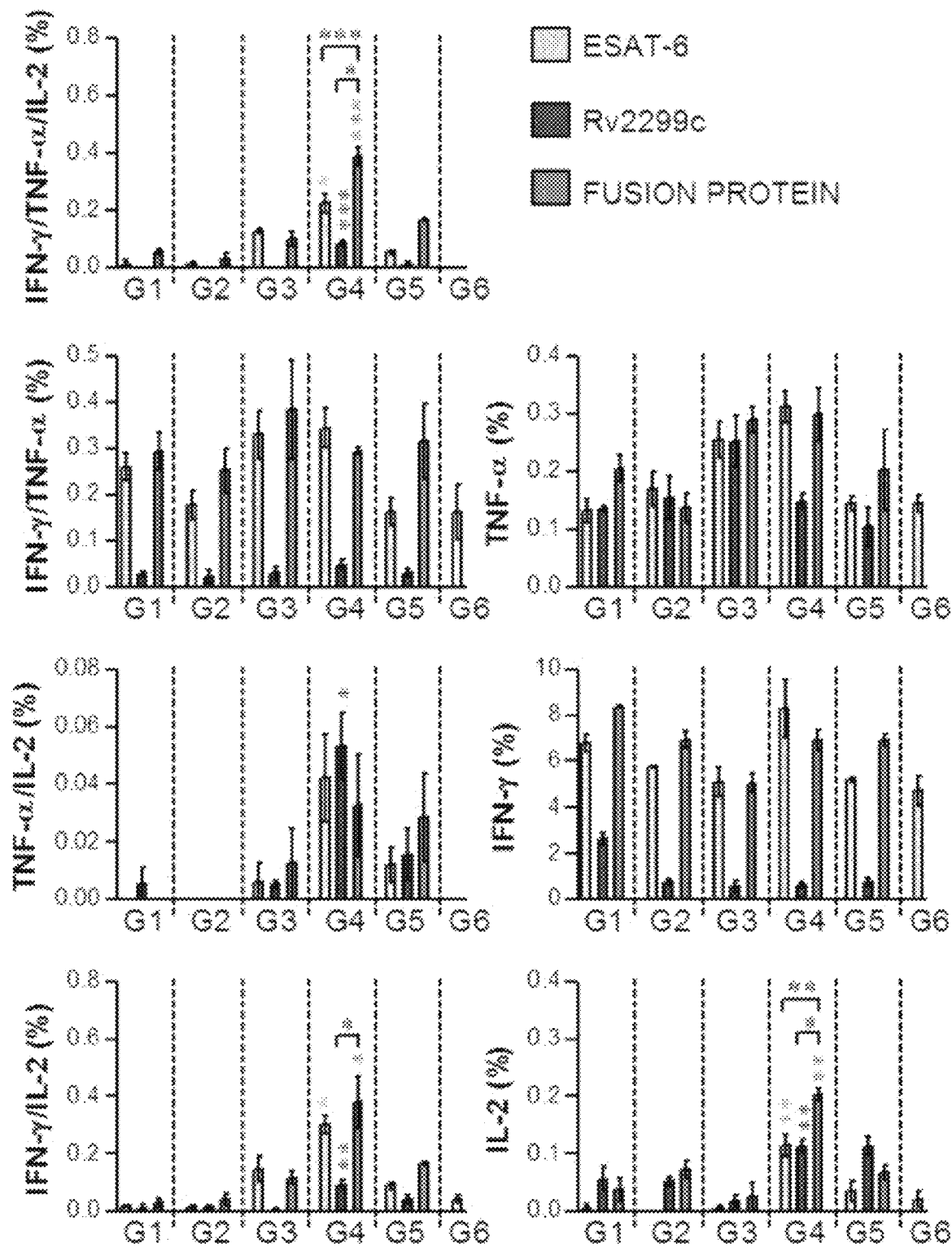
Figure 11B:
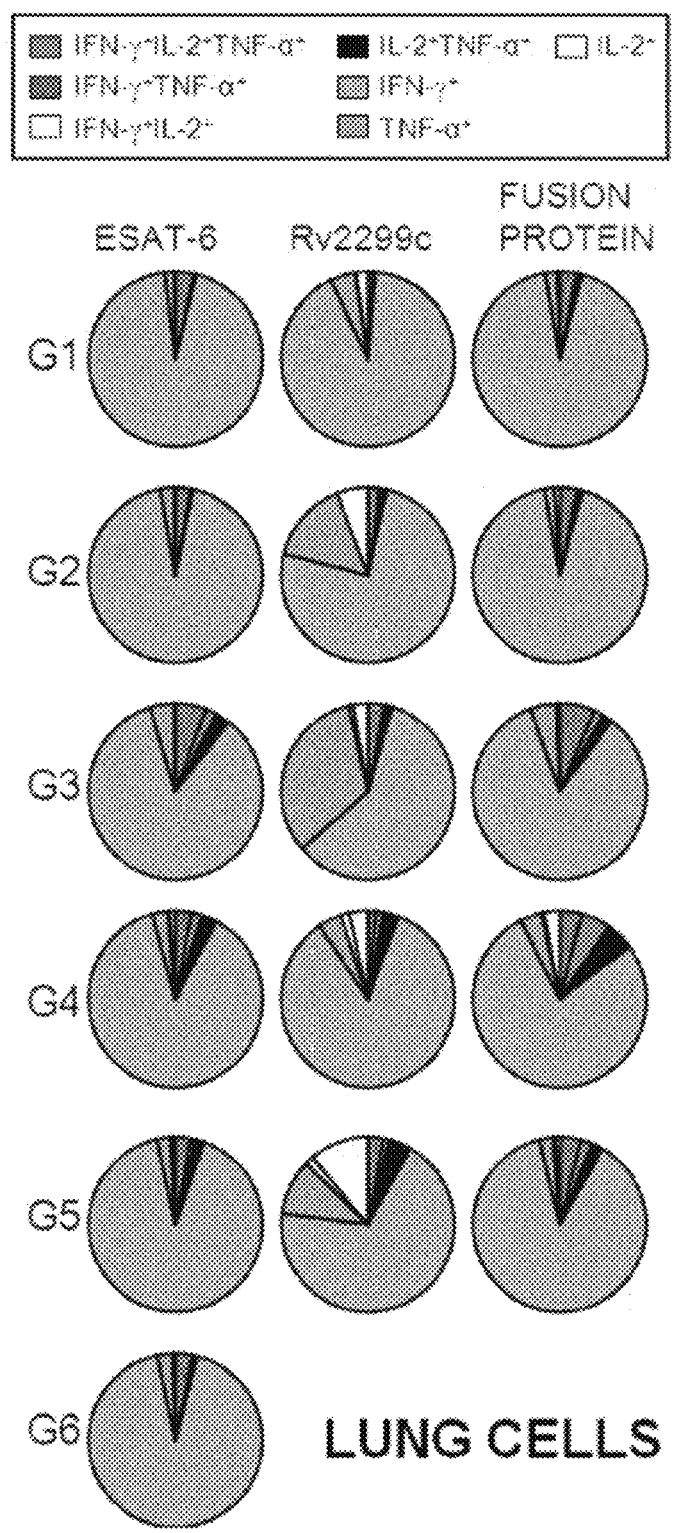
Figure 12A:
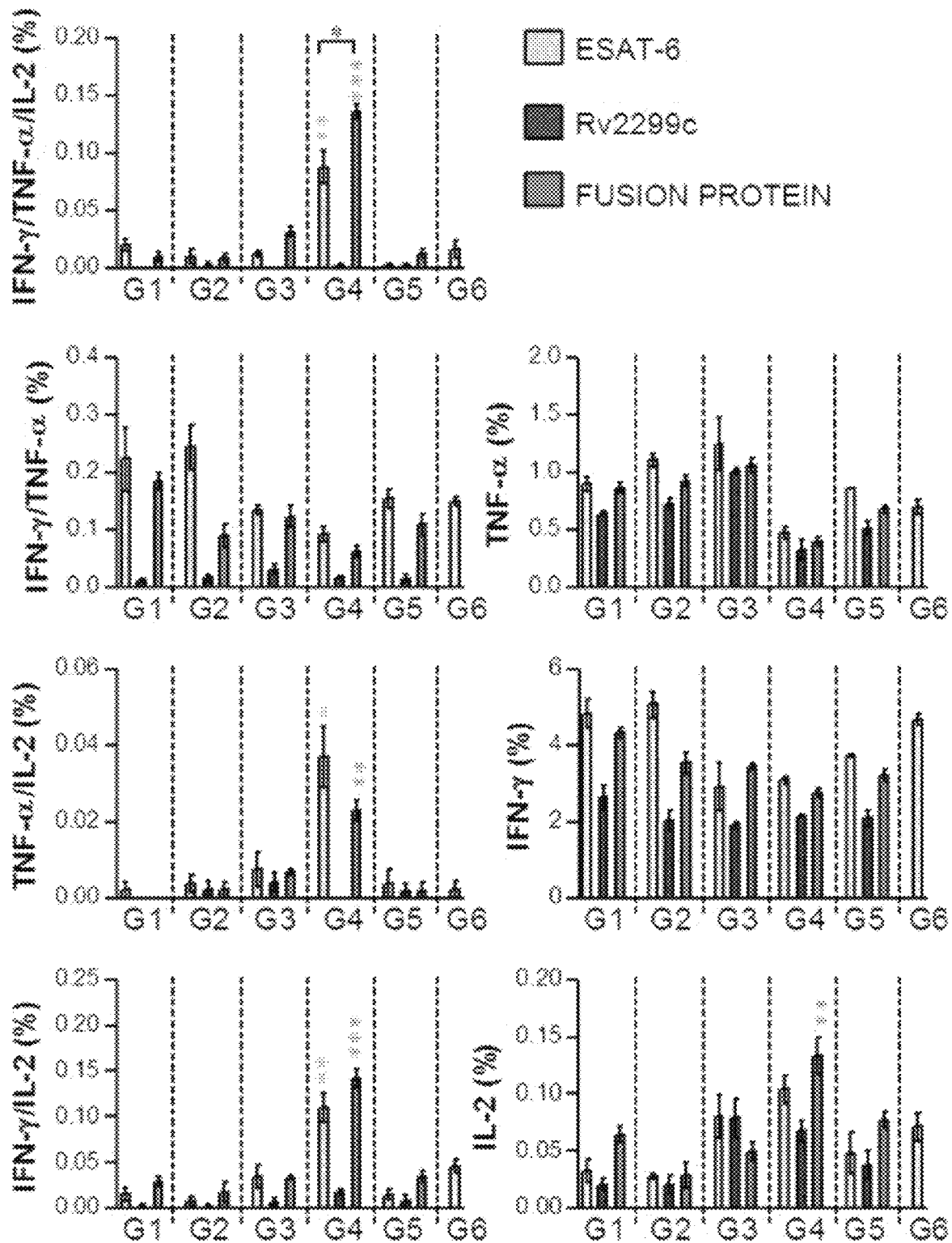
Figure 12B:
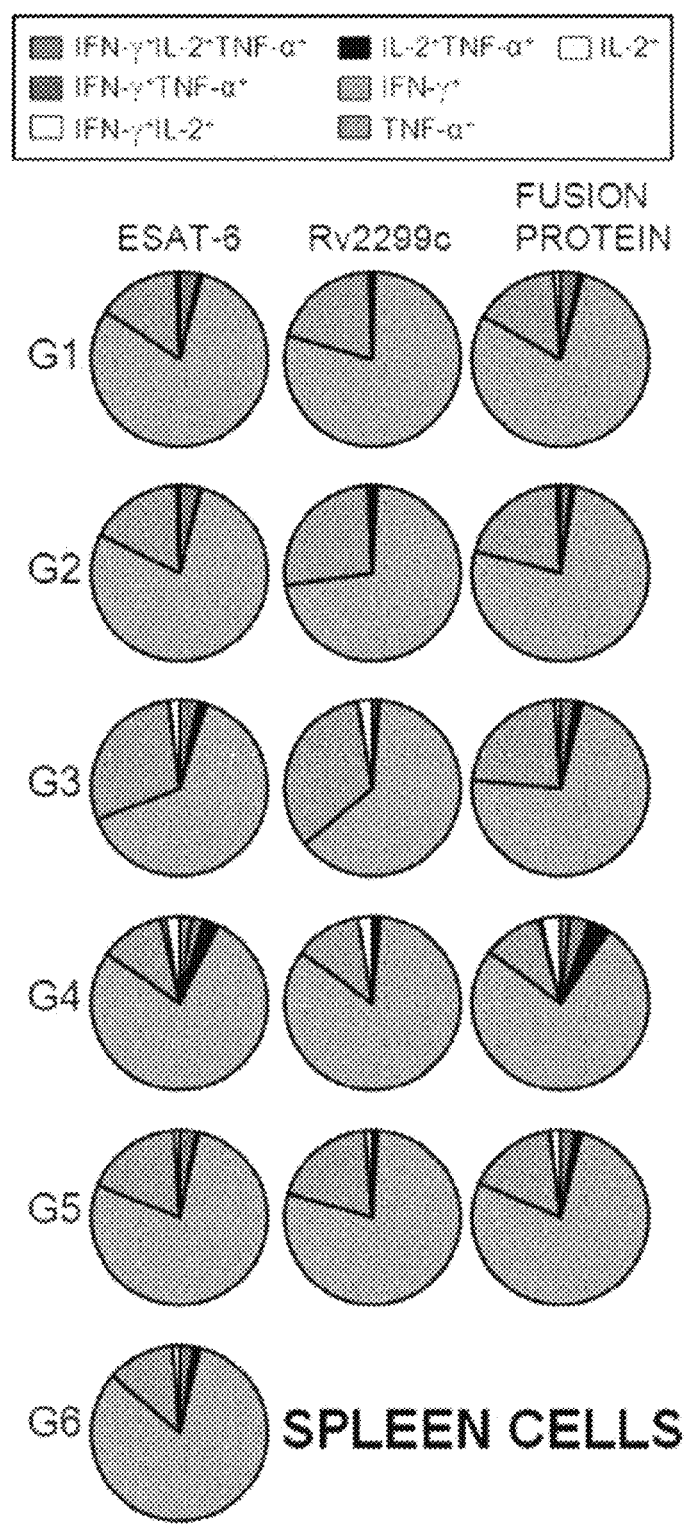

Th1-mediated immune responses and multifunctional T cells play an important role in prophylactic immunity against Mtb. Thus, the changes in T cell phenotype induced by Rv2299c+ESAT-6 fusion protein-vaccination was next evaluated. At 16 weeks after the challenge, lung cells (See FIGS. 11A and 11B) and spleen cells (See FIGS. 12A and 12B) were isolated and stimulated with each immunizing antigen, and the phenotype of CD4+ T cells reacted was evaluated by multicolor intracellular cytokine staining. Compared to other groups, triple positive CD4+ T cells (IFN-γ, TNF-α and IL-2 co-expression) in the lungs were increased and maintained only in the Rv2299c+ESAT-6 fusion protein-vaccinated group (See FIGS. 11A, 11B, 12A, and 12B). Further, an increased frequency of double-positive multifunctional CD4+ T cells (TNF-α+IL-2+CD4+ T cells) after the challenge was shown in the Rv2299c+ESAT-6 fusion protein-vaccinated group (See FIGS. 11A, 11B, 12A, and 12B).

Example 11

Consideration

It was found that subunit protein vaccines are potentially useful in boosting BCG replacement or BCG-induced immune responses (Dalmia and Ramsay, 2012). A new vaccine development strategy is proposed to improve the preventive effect of TB vaccine candidates. Selecting the optimal antigen to include a multi-protein vaccine is the most important step in vaccine development. DCs regulate subsequent development of Th1 or Th2 types in naive T cell polarization and lymph node drainage. Thus, DC-activated protein-based vaccines can improve the prophylactic immunity of other antigens produced. In this study, it is found that the Rv2299c protein capable of activating DCs is a valuable target for the development of a TB vaccine. This indicates that the Rv2299c+ESAT-6 fusion protein significantly reduces the bacterial load of lungs after the challenge with highly virulent Mtb HN878 clinical strains.

The basic principle of TB vaccine development designed to induce T-cell-based immunity is based on the assumption that the strong Th1 response specifically against the tuberculosis antigens is the essential mechanism of anti-tuberculosis immunity. Antigens that do not induce the Th1 response do not have a vaccine efficacy against Mtb, but not all of the proteins that induce a strong Th1 response elicit a significant protective effect (Orr et al., 2014). The MVA85A vaccine, which elicits a robust Th1 response against Ag85A, does not show a pronounced BCG boosting effect in humans (Tameris et al., 2013). It is important that the vaccine induces a memory T cell response and induces a long-term immune response. DCs play a critical role in effective activation of T cells and the induction of memory T cell responses. It is known that mice vaccinated with Mtb-infected DCs (Tascon et al., 2000) or antigen extract-treated DCs (Rubakova et al., 2007) are protected against Mtb infection. These results support the strategy development of an anti-tuberculosis vaccine that targets in vivo DCs (Sinha et al., 2007). In this study, in order to test the hypothesis that DC-activated proteins are potential vaccine candidates, it is an important research question to choose a reliable DC-activated protein. First, mycobacterial HSPs are selected because mycobacterial HSPs are associated with an ability to activate immune cell DCs such as macrophages and DCs (Wang et al., 2001, Wang et al., 2002, Franco et al., 2008) and adjuvant activity (Srivastava et al., 1998). This study reveals that Rv2299c (HSP90) among mycobacterial HSPs induce DC maturation through TLR4 signaling and MAPK and NF-κB activation. This activation leads to an increase in the expression of co-stimulatory molecules promoting Th1-type immune responses and the secretion of proinflammatory cytokines. Recently, it has been reported that DCs isolated from spleen cells of mice treated with Rv2299c result in increased expression of MHC molecules and co-stimulatory molecules and DC-loaded tumor antigens with Rv2299c treatment induce an increased anti-tumor immunity effect (Vo et al., 2015). These results and our study results suggest that Rv2299c has adjuvant activity through DC activation in vivo and ex vivo.

It was reported that several mycobacterial proteins activate DCs to induce Th1 infection response through the TLR2 pathway (Bansal et al., 2010a, Byun et al., 2012a) or the TLR4 pathway (Choi et al., 2015, Kim et al., 2013), or to induce Th2 infection response (Bansal et al., 2010b) through TLR2 pathway (Bansal et al., 2010b). This indicates that each antigen has different activity in dendritic cells. Recombinant mycobacterial HSP70 is signaled through both TLR4 and TLR2, whereas mycobacterial HSP65 is signaled through TLR4 alone to activate immune cells (Bulut et al., 2005). Human HSP90 elicits biological activity through the TLR4 pathway (Thuringer et al., 2011, Hutchinson et al., 2009). This study demonstrates that Rv2299c of the HSP90 family activates DCs in a TLR4-, MyD88- and TRIF-dependent manner This is demonstrated by pulldown analysis and experiments using TRL4 or TRL2 knockout mice.

It is assumed that it is important to activate T cells with anti-mycobacterial activity for a reliable DC-based vaccine. However, there is little known about the actual anti-mycobacterial effect elicited by the DC-activated protein which induces the Th1 immune response. This study demonstrates that T cells activated by Rv2299c-mature DC significantly inhibit Mtb growth in macrophages and induce large amounts of cytokine production compared to inactivated T cells. T cells activated non-specifically by LPS-matured DCs exhibited no anti-bactericidal activity. These results demonstrate that Rv2299c induces specific activation of naive CD+T cells with prophylactic activity.

It has been reported that a subunit vaccine consisting of two to four fusion protein antigens induces a strong preventive response and effect equivalent to prevention induced only by BCG. Most people are vaccinated with BCG at infancy, but their efficacy diminishes over time (Bertholet et al., 2010). Thus, boosting BCG-induced prophylactic immunity may be the most practical strategy. Therefore, the prophylactic immune response and effects of fusion proteins composed of Rv2299c and ESAT-6 are investigated. ESAT-6 is selected as a fusion partner because ESAT-6 is one of the major antigens included in the vaccine in current clinical trials. In this study, mice inoculated with fusion protein showed similar efficacy as mice inoculated with BCG alone. It has been suggested that memory T cell recall responses do not depend on DCs, and other untechnical antigen-presenting cells may be sufficient for the initiation of secondary responses (Bertram et al., 2004, Dawicki and Watts, 2004), whereas other studies have demonstrated that activation of memory T cells mainly depends on DC in response to systemic or local infection (Zammit et al., 2005; Wakim et al., 2008). In this study, it is found that Rv2299c-mature DCs induce the effect/memory CD4+ T cells expansion obtained from Mtb-infected mice. These suggest that Rv2299c can induce a memory T cell recall response in BCG-vaccinated subjects. Boosting BCG with the Rv2299c-fused ESAT-6 protein reduces pathology and provides long-term protection against Mtb compared to BCG alone. In particular, since BCG vaccination on mouse provides less protection against W-Beijing isolation compared to Mtb H37Rv, the effect of the fusion protein on the Mtb HN878, a virulent clinical strain obtained in the W-Beijing family is determined (Lopez et al., 2003). This isolation causes death and extensive lung pathology in infected C57BL/6 mice.

The preventive effect of the Rv2299c+ESAT-6 fusion protein vaccine is examined against the Mtb HN878 strain, a highly virulent W-Beijing strain, in the mouse model. Rv2299c+ESAT-6 fusion protein-immunized mice were substantially prevented after challenging the Mtb HN878 strain according to lung pathology and bacterial growth assessment (See FIG. 10). Rv2299c+ESAT-6 fusion vaccination showed significantly reduced bacterial burden in the lung as well as markedly reduced lung pathology, thereby exhibiting remarkable prevention against Mtb HN878.

In general, vaccine-induced prevention against Mtb infection is particularly associated with Ag-specific multifunctional IFN-γ$^+$TNF-α$^+$IL-2$^+$ and TNF-α$^+$IL-2$^+$ CD4$^+$ T cells in the lungs. Importantly, testing for Ag-immunized mice exhibits that immunization against the Rv2299c+ESAT-6 fusion protein remarkedly induces production of multifunctional CD4$^+$ T cells in the lungs in pre-challenge and post-challenge (See FIGS. 11 and 12). Based on this trend, Rv2299c may serve as the main element of a successful vaccine against Mtb infection. Rv2299c+ESAT-6 fusion immunization, other than BCG alone or protein alone immunization, induced Rv2299c-ESAT-6 protein-specific multifunctional CD4$^+$ T cell response in the lung. The ability of the vaccine candidate to induce Rv2299c+ESAT-6 fusion-specific multifunctional T cell responses in the lung after the intramuscular injection is consistent with the prophylactic effect observed. Further, this response induced by Rv2299c+ESAT-6 fusion protein immunization was maintained for up to 16 weeks post-infection. This suggests that they significantly increase after recognition of Mtb infection with prime multifunctional memory CD4$^+$ T cells. These results may indicate that it is important to suitably subserve vaccine candidates to induce prevention of lung immune responses.

In conclusion, these results suggest that Rv2299c is an excellent candidate for the rational design of multi-antigen effective TB vaccines. Therefore, more detailed studies are required to examine the specific vaccine efficacy and effective prevention mechanisms of the Rv2299c+ESAT-6 fusion protein in murine or guinea pig models.

| Rv2299c amino acid sequence |
|---|
| (SEQ. ID. No. 1) |
| MNAHVEQLEFQAEARQLLDLMVHSVYSNKDAFLRELISNASDALDKLRIE |
| ALRNKDLEVD |
| TSDLHIEIDADKAARTLTVRDNGIGMAREEVVDLIGTLAKSGTAELRAQL |
| REAKNAAASE |
| ELIGQFGIGFYSSFMVADKVQLLTRKAGESAATRWESSGEGTYTIESVED |
| APQGTSVTLH |
| LKPEDAEDDLHDYTSEWKIRNLVKKYSDFIAWPIRMDVERRTPASQEEGG |
| EGGEETVTIE |
| TETLNSMKALWARPKEEVSEQEYKEFYKHVAHAWDDPLEIIAMKAEGTFE |
| YQALLFIPSH |
| APFDLFDRDAHVGIQLYVKRVFIMGDCDQLMPEYLRFVKGVVDAQDMSLN |
| VSREILQQDR |
| QIKAIRRRLTKKVLSTIKDVQSSRPEDYRTFWTQFGRVLKEGLLSDIDNR |
| ETLLGISSFV |
| STYSEEEPTTLAEYVERMKDGQQQIFYATGETRQQLLKSPHLEAFKAKGY |
| EVLLLTDPVD |
| EVWVGMVPEFDGKPLQSVAKGEVDLSSEEDTSEAEREERQKEFADLLTWL |
| QETLSDHVKE |
| VRLSTRLTESPACLITDAFGMTPALARIYRASGQEVPVGKRILELNPSHP |
| LVTGLRQAHQ |
| DRADDAEKSLAETAELLYGTALLAEGGALEDPARFAELLAERLARTL |

The invention claimed is:

1. A composition for inducing maturation of dendritic cells, the composition comprising a fusion protein of Rv2299c and ESAT-6 as an active ingredient.

2. The composition of claim 1, wherein the Rv2299c is a protein derived from *M. tuberculosis*.

3. The composition of claim 1, wherein the fusion protein of Rv2299c and ESAT-6 is included at a concentration of 1 μg/ml to 20 μg/ml.

4. A method for inducing maturation of immature dendritic cells, the method comprising:

treating immature dendritic cells with a fusion protein of Rv2299c and ESAT-6 to mature the immature dendritic cells into mature dendritic cells.

5. The method of claim 4, wherein after treating the immature dendritic cells with the fusion protein of Rv2299c and ESAT-6, the cells are cultured for 12 hours to 36 hours.

6. The method of claim 4, wherein the fusion protein of Rv2299c and ESAT-6 increases the production of at least one selected from the group consisting of TNF-α, IL-12p70, IL-6 and IL-1β during the maturation of immature dendritic cells.

7. The method of claim 4, wherein the fusion protein of Rv2299c and ESAT-6 is included at a concentration of 1 μg/ml to 20 μg/ml.

8. The method of claim 4, wherein the maturation of the immature dendritic cells is caused by stimulation of TLR (toll-like receptor)-4 with the fusion protein of Rv2299c and ESAT-6.

9. The method of claim 4, wherein the maturation of immature dendritic cells is caused by stimulation of mitogen-activated protein kinase (MAPK) and NF-κB.

10. A composition for enhancing immunity, the composition comprising the composition of claim 1.

11. A composition for enhancing immunity, the composition comprising the composition of claim 2.

* * * * *